US008934956B2

(12) United States Patent
Glenn et al.

(10) Patent No.: US 8,934,956 B2
(45) Date of Patent: Jan. 13, 2015

(54) INTRAVASCULAR ELECTRODES AND ANCHORING DEVICES FOR TRANSVASCULAR STIMULATION

(75) Inventors: Richard A. Glenn, Santa Rosa, CA (US); Jeffrey A. Smith, Petaluma, CA (US); Geoffrey A. Orth, Sebastopol, CA (US); Kevin Holbrook, Santa Rosa, CA (US); Michael S. Williams, Santa Rosa, CA (US)

(73) Assignee: Interventional Autonomics Corporation, Chapel Hill, NC (US)

( * ) Notice: Subject to any disclaimer, the term of this patent is extended or adjusted under 35 U.S.C. 154(b) by 56 days.

(21) Appl. No.: 13/281,399

(22) Filed: Oct. 25, 2011

(65) Prior Publication Data
US 2013/0018247 A1    Jan. 17, 2013

Related U.S. Application Data

(63) Continuation-in-part of application No. PCT/US2011/001535, filed on Sep. 1, 2011, and a continuation-in-part of application No. 13/068,866, filed on Jul. 11, 2011, now abandoned.

(60) Provisional application No. 61/378,925, filed on Aug. 31, 2010.

(51) Int. Cl.
    *A61B 5/04*    (2006.01)
    *A61N 1/05*    (2006.01)
    *A61B 5/00*    (2006.01)
    (Continued)

(52) U.S. Cl.
    CPC ............... *A61N 1/05* (2013.01); *A61B 5/6862* (2013.01); *A61B 5/0422* (2013.01); *A61N 1/057* (2013.01)

USPC .......... 600/381; 600/374; 600/508; 607/116; 607/119

(58) Field of Classification Search
    CPC ... A61N 1/0558; A61N 1/057; A61N 1/0573; A61N 1/362; A61N 1/0476; A61N 1/059; A61B 8/1492; A61B 5/6876; A61B 5/6858; A61B 5/04085; A61B 5/6852; A61B 2018/00267; A61M 25/04; A61M 2025/0293; A61M 2039/0261; A61M 2039/0279
    USPC ......... 600/372–375, 377, 381, 393, 508–510; 607/44, 116
    See application file for complete search history.

(56) References Cited

U.S. PATENT DOCUMENTS 6,240,307 B1 *  5/2001  Beatty et al. ................. 600/374
6,837,886 B2 *  1/2005  Collins et al. .................. 606/41
(Continued)

*Primary Examiner* — Linda Dvorak
*Assistant Examiner* — Brian M Antiskay

(57) ABSTRACT

An intravascular electrode device for use in neuromodulation includes an anchor expandable from a radially compressed position to a radially expanded position. A lead extends from the anchor and has at least one conductor extending through it. A flex circuit is coupled to the anchor and comprises a flexible insulative substrate, a plurality of electrodes carried by the substrate, and a plurality of conductive traces carried by the substrate, each trace electrically coupled to an electrode and a conductor. Expansion of the anchor within a blood vessel biases the electrodes into contact with the surrounding blood vessel wall. An exemplary anchor includes a first portion having expansion forces sufficient to bias the electrodes against the vessel wall for mapping and chronic stimulation, and a second portion having greater radial expansion forces sufficient to chronically engage the vessel wall once an optimal electrode location has been selected.

11 Claims, 22 Drawing Sheets

(51) Int. Cl.
*A61B 5/042* (2006.01)
*A61B 5/02* (2006.01)
*A61N 1/00* (2006.01)

(56) References Cited

U.S. PATENT DOCUMENTS

| | | | |
|---|---|---|---|
| 7,925,352 B2 | 4/2011 | Stack et al. | |
| 8,109,895 B2* | 2/2012 | Williams et al. | 604/8 |
| 8,369,954 B2 | 2/2013 | Stack et al. | |
| 8,412,350 B2* | 4/2013 | Bly | 607/116 |
| 8,428,730 B2 | 4/2013 | Stack et al. | |
| 2005/0234431 A1* | 10/2005 | Williams et al. | 604/890.1 |
| 2006/0058598 A1* | 3/2006 | Esposito | 600/374 |
| 2007/0255379 A1* | 11/2007 | Williams et al. | 607/120 |
| 2007/0265687 A1* | 11/2007 | Deem et al. | 607/72 |
| 2010/0023088 A1* | 1/2010 | Stack et al. | 607/44 |
| 2010/0197994 A1* | 8/2010 | Mehmanesh | 600/18 |

\* cited by examiner

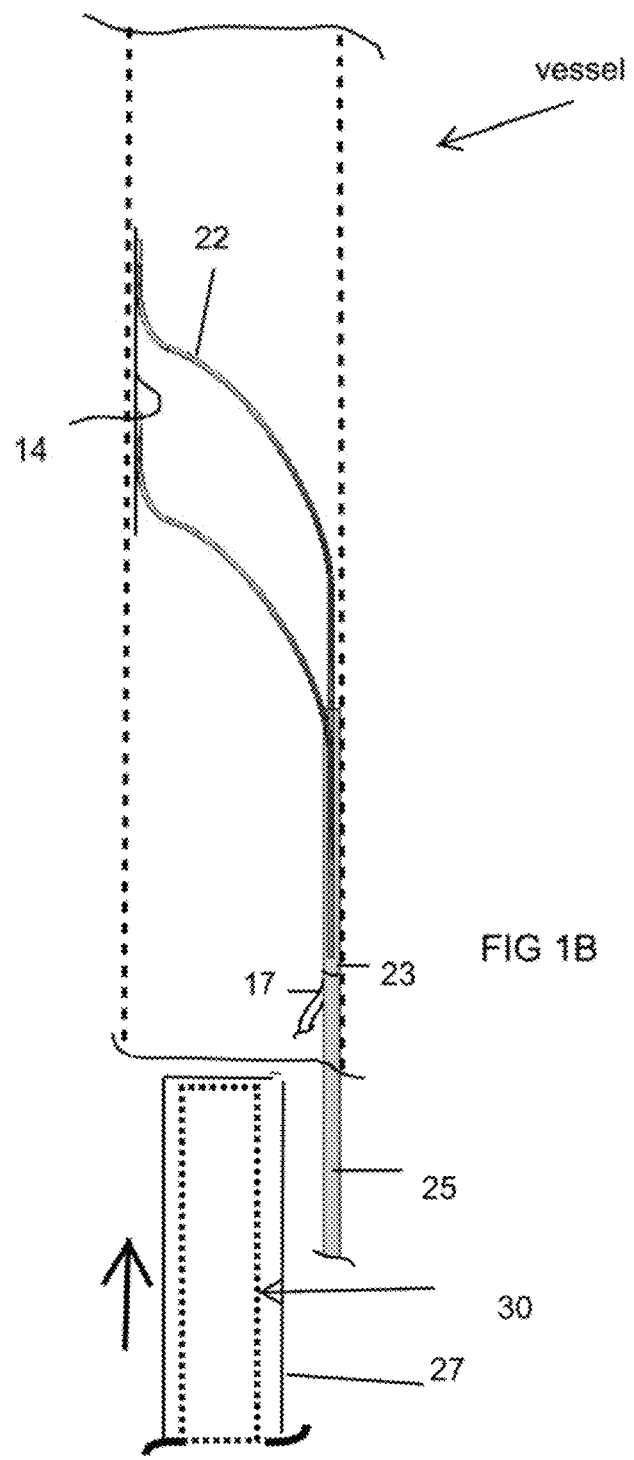

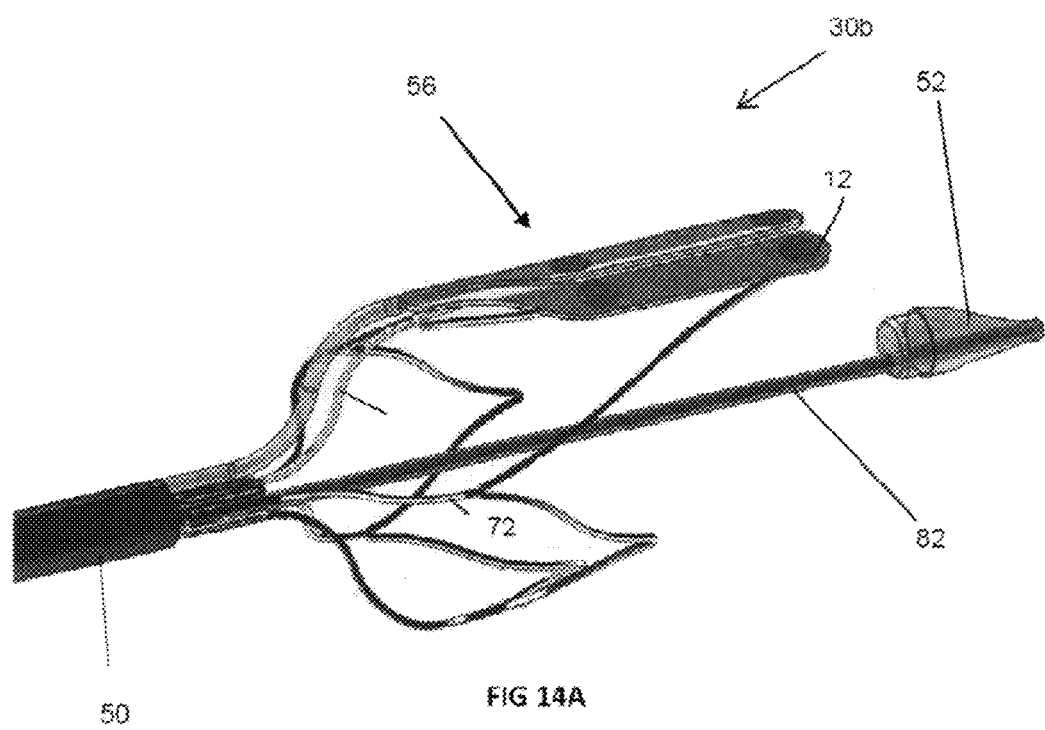

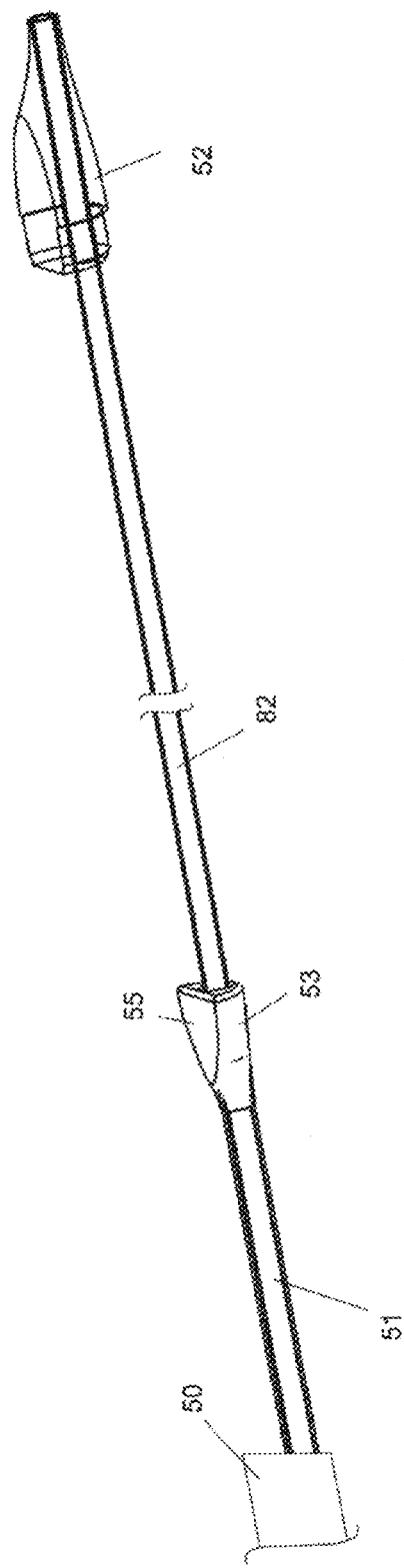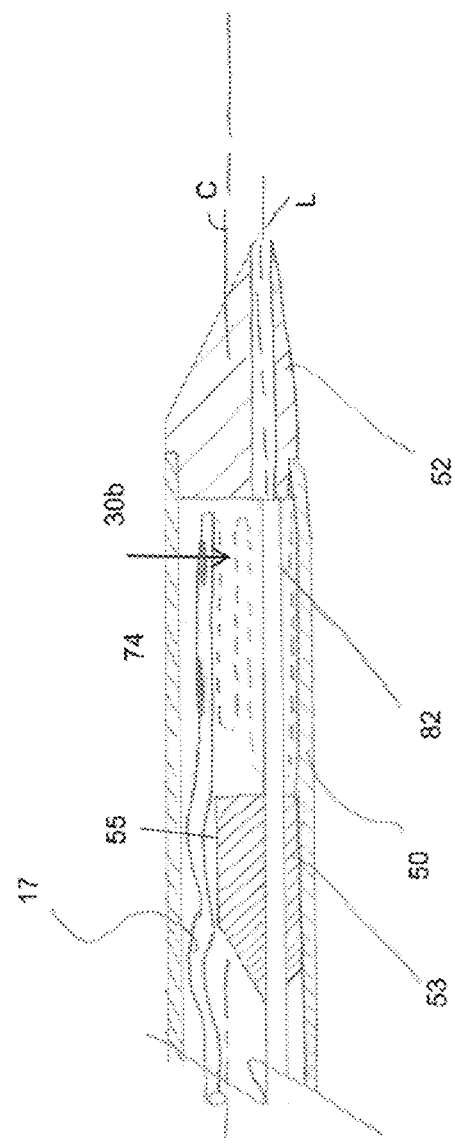

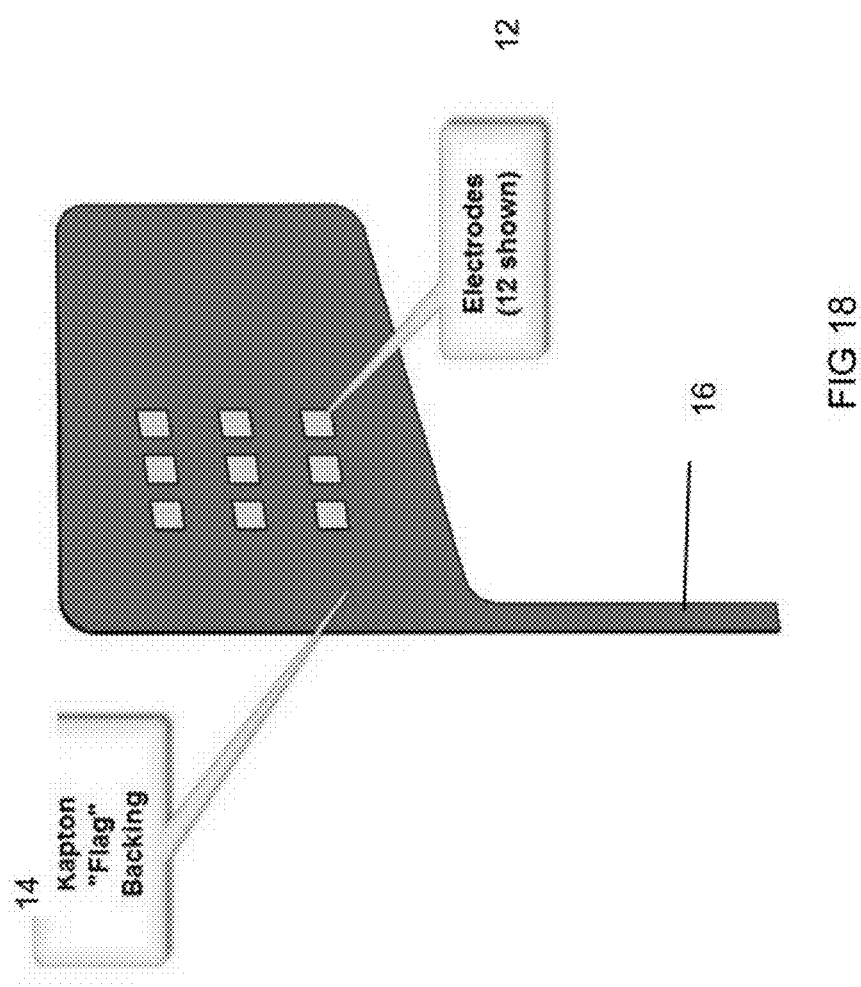

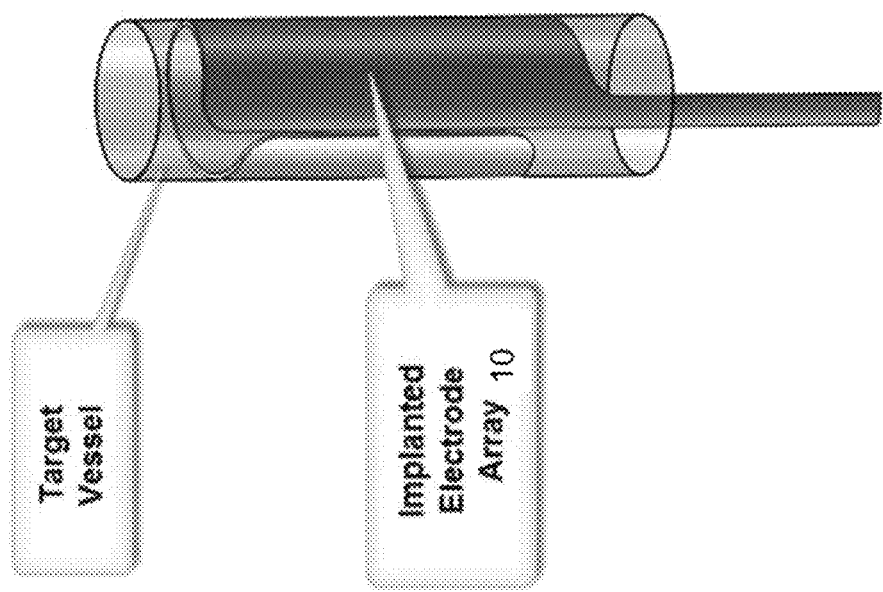

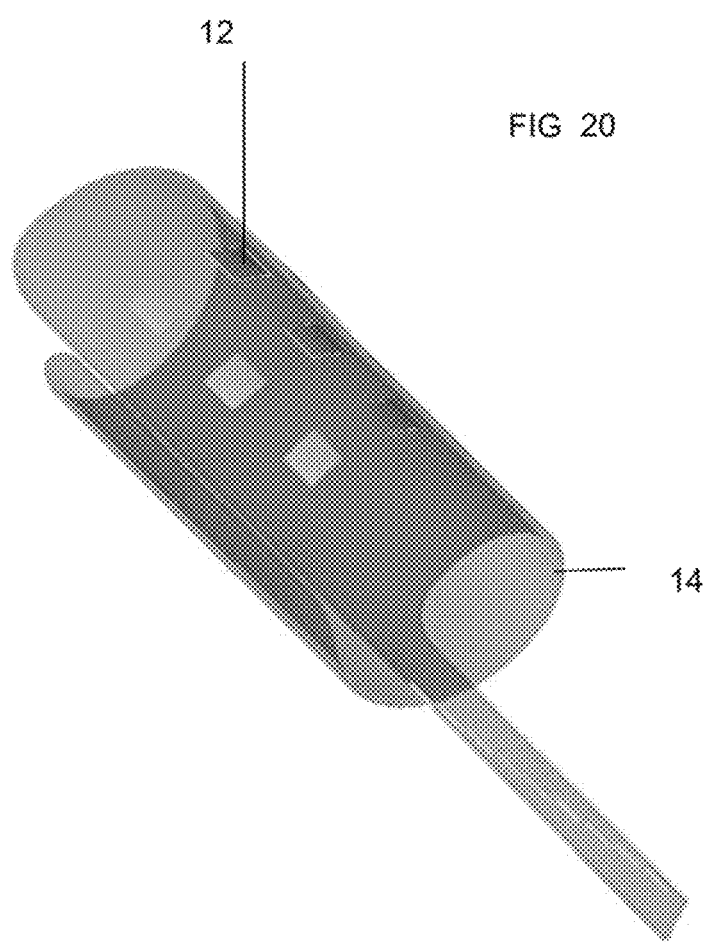

INTRAVASCULAR ELECTRODES AND ANCHORING DEVICES FOR TRANSVASCULAR STIMULATION

This application is a continuation-in-part of claims the benefit of U.S. application Ser. No. 13/068,866, filed Jul. 11, 2011. This application also claims the benefit of U.S. Provisional Application No. 61/378,925, filed Aug. 31, 2010, and is a continuation-in-part of PCT/US2011/001535, filed Sep. 1, 2011. Each of the aforementioned applications is incorporated herein by reference.

TECHNICAL FIELD OF THE INVENTION

The present application generally relates to intravascular electrodes, anchors, and associated systems and methods used for delivering therapy to nervous system targets.

BACKGROUND

Applicants' prior Application Publication No. U.S. 2007/0255379, discloses an intravascular neurostimulation device and associated methods for using the neurostimulation device to stimulate nervous system targets. In various ones of the disclosed embodiments, electrodes positioned within a blood vessel (e.g. a jugular vein, superior vena cava, or inferior vena cava) are used to transvascularly stimulate nervous system targets located outside the vasculature. Such stimulation can be used to lower heart rate and/or control blood pressure as a treatment for hypertension or heart failure (HF). Anchors are described for maintaining the electrodes in contact with the blood vessel wall. The anchors include structural features that allow the anchor to radially engage a vessel wall. As described, a band, sleeve, mesh or other framework formed of one or more shape memory (e.g. nickel titanium alloy, nitinol, thermally activated shape-memory material, or shape memory polymer) elements or stainless steel, Elgiloy, or MP35N elements may be used as an anchor. In use, the anchor (with the electrodes thereon) may be released from a sheath within the blood vessel, such that the anchor expands into contact with the blood vessel and thereby biases the electrodes against the vessel wall.

Applicants' co-pending application Ser. No. 12/413,495, filed Mar. 27, 2009 and entitled SYSTEM AND METHOD FOR TRANSVASCULARLY STIMULATING CONTENTS OF THE CAROTID SHEATH discloses a method for transvascularly stimulating the vagus nerve and other nervous system structures, such as those disposed within the carotid sheath. The disclosed method includes advancing an energy delivery element, which may be an electrode, into an internal jugular vein, retaining the energy delivery element in a portion of the internal jugular vein contained within a carotid sheath, and energizing the energy delivery element to transvenously direct energy to target contents of the carotid sheath external to the internal jugular vein. The energy may be directed to a carotid artery within the carotid sinus sheath, and/or to a carotid sinus nerve or nerve branch within the carotid sinus sheath, to nerve branches emanating from carotid artery baroreceptors, and/or to a vagus nerve or associated nerve branch within the carotid sinus sheath. In some of the disclosed embodiments, a bi-lateral system is employed, in which a second electrode or other second energy delivery element is introduced into a second internal jugular vein and retained in a portion of the second internal jugular vein contained within a second carotid sheath. The second energy delivery element is energized to direct energy to contents of the second carotid sheath external to the second internal jugular vein.

The right vagus nerve primarily innervates the sinoatrial node of the heart; stimulation of this nerve increases the duration of the cardiac cycle. The left vagus nerve primarily innervates the atrioventricular (AV) node of the heart; stimulation of this nerve slows AV conduction. The assignee of this application conducted anatomical studies on human cadavers to investigate the relative location of the right vagus nerve to veins that could provide sites for transvenous vagal stimulation to reduce heart rate and blood pressure. The findings strongly support the rationale for a transvenous approach to vagus nerve stimulation in the human. The right vagus nerve and its cardiac branches closely and reliably course directly alongside the largest veins in the neck and superior mediastinum, namely the right internal jugular vein, right brachiocephalic vein, superior vena cava, and azygotic arch. Additional studies performed by this assignee support the use of electrodes against the posterior wall of the mid- to cephalic superior vena cava to control heart rate and blood pressure, such as for treatment of heart failure.

BRIEF DESCRIPTION OF THE DRAWINGS

FIG. 1B is a side elevation view showing the array and anchor of FIG. 1A schematically disposed within a blood vessel.

FIG. 14A illustrates the system of FIG. 11A with the first portion of the anchor deployed in the mapping position.

FIG. 14C is a perspective view of the distal ends of the sheath, tubular shaft and small diameter tube used for deploying the system of FIG. 11A.

FIG. 14D is a longitudinal cross section showing the anchor, electrodes and leads assembled with the deployment system shown in FIG. 14C.

FIG. 18 shows an alternative substrate and electrode configuration that may be used for transvascular stimulation.

FIG. 19 schematically shows the FIG. 18 embodiment in a curled position within a vessel.

FIG. 20 is similar to FIG. 19 but does not show the vessel.

DETAILED DESCRIPTION

The present application describes designs of intravascular electrodes that may be positioned within a blood vessel and used for transvascular stimulation of nervous system targets outside the blood vessel. Also described are anchors suitable for temporarily holding the electrodes in contact with the vessel wall while mapping is performed to identify the optimal site for electrode placement, as well as anchors suitable for chronically retaining the electrodes at the optimal site once determined. The electrodes and anchors may be deployed within various blood vessels for stimulating various nerves or other nervous system targets, which vessels and targets may include but are not limited those described herein.

The disclosed electrodes, anchors and associated components are suitable for use in neuromodulation systems which may also include sensors, a power supply, control and power generation circuitry, a programmer and various other features including those described in the referenced applications. Such systems may be fully intravascular systems of the type wherein both the electrodes and pulse generator are located within the vasculature, or systems where the pulse generator is subcutaneously placed or located outside the body.

First Embodiment

Figure 1A:
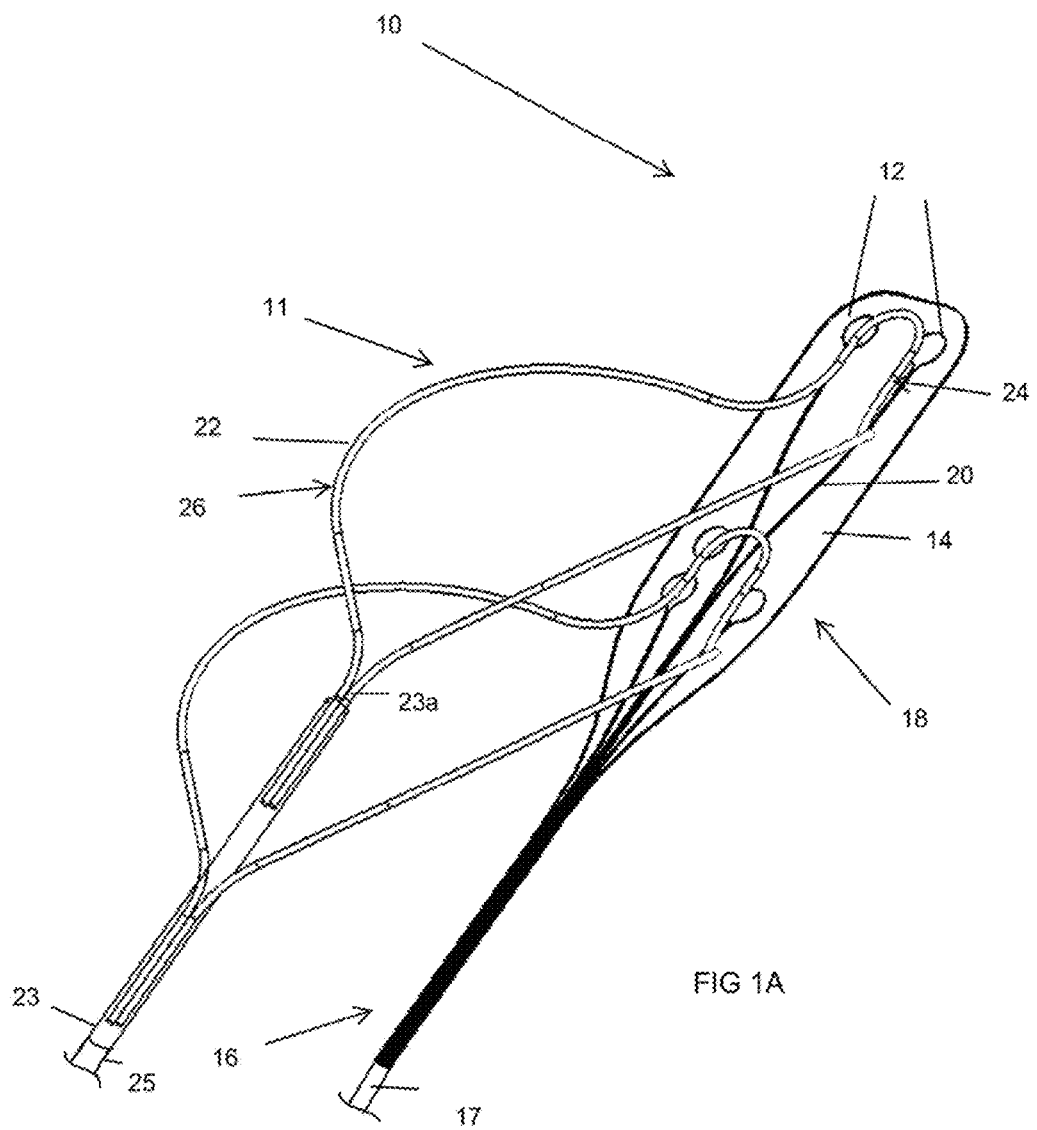
FIG. 1A is a perspective view showing a first embodiment of an electrode array together with a temporary anchor for use during mapping.

FIG. 1A illustrates a first embodiment of an electrode array and anchoring system 10 that is positionable within a blood vessel (such as the vessels discussed herein). The array is coupled to an intravascular, subcutaneous, or extracorporeal pulse generator (not shown), forming a system for use in transvascular stimulation.

System 10 includes an electrode array comprising a plurality of electrodes 12 positioned on a flexible substrate 14. Four electrodes are shown in a 2×2 array, although various electrode numbers and arrangements may be used. In one embodiment, the left distal and proximal electrodes are longitudinally aligned with one another, and the right distal and proximal electrodes are longitudinally aligned with one another. The left and right electrodes may be circumferentially aligned, such that the left distal electrode is circumferentially aligned with the right distal electrode and the left proximal electrode is circumferentially aligned with the right proximal electrode. In alternate embodiments the left and right electrodes may be longitudinally off-set from one another rather than longitudinally aligned. For example, the left electrodes (distal and proximal) might be more proximal than their right electrode counterparts. This latter arrangement gives the array a larger capture area for delivery of stimuli and thus facilitating delivery of stimulus to a nerve that might be helically coiled around the blood vessel within which the electrodes are located.

The substrate includes a relatively narrow portion 16, and a broader portion 18 (which may be paddle-like as shown) on which the electrodes are positioned. Although the longitudinal axes of the narrow and broader portions 18 are longitudinally aligned, in alternative embodiments the broader portion 18 may be positioned asymmetrically relative to the longitudinal axis of the narrow portion. Substrates and electrodes for alternative embodiments of this type are illustrated in FIGS. 18-20.

The electrodes are disposed at one face of the substrate 14—preferably the face that faces the vessel wall when the system is implanted—such that the active electrode surfaces are in contact with the vessel wall and the substrate provides an electrically insulative backing and electrically isolates the electrodes from one another. The electrodes may be deposited or printed onto the substrate, or they may be positioned in or molded into the substrate or openings formed through the substrate. Conductors or conductive traces 20 are formed, deposited, printed on or molded into/onto the substrate. The conductors 20 extend proximally from each of the electrodes 12, terminating at contacts near the proximal end of the narrow portion 16. A lead 17, which may be formed of tubing, shrink material, or other suitable material, is disposed over at least a portion of narrow portion 16, and includes conductors electrically coupled to the contacts of the conductors or traces 20.

The substrate is preferably a material that provides an electrically insulative backing to the electrodes. The material might be one capable of bending or curving relative to the vessel's longitudinal axis to approximately match or conform to the curvature of a blood vessel wall when held in contact with the wall by an anchor. The substrate may similarly be placed in a curved position when disposed within a delivery sheath for introduction into the vasculature.

The substrate 14 may be a flex circuit formed of polyimide or other suitable materials. Alternate materials that may be used for the substrate include, but are not limited to, polyurethane, polyethylene, silicone rubber, fluoropolymer, stainless steel, platinum-iridium, MP35N, titanium and other biocompatible metals/polymers/elastomers.

In some embodiments, all or a portion of the substrate may be of a type that resorbs or degrades over time, as tissue growth (e.g., cellular encapsulation, in-growth, endothelialization) begins to retain the electrodes in position. Materials suitable for this use include, but are not limited to, polylactide (PLA), polyglycolide (PGA) and their copolymer (PGLA). In such embodiments, the electrodes may be provided with non-degradable insulating material on the portions of the electrodes which are not intended for contact with the vessel wall, such that the insulating material remains intact following resorption or degradation of the substrate.

In other embodiments, the flex circuit may be coated to improve its biocompatibility, to improve its insulative properties, and/or to reduce the body's response to a foreign substance. One preferred substrate is formed of polyethylene or polyimide and has a covering or coating of silicone or polyurethane over the substrate and the conductors while leaving the electrodes themselves exposed.

For electrode array implantation, it is desirable for the user to be able to empirically select an electrode location by positioning the electrode array, delivering stimulation from the selected location, measuring the response, and then repeating the process with the electrodes at one or more different locations within the blood vessel. This mapping process allows the user to evaluate the response at various stimulation sites, so s/he may select the most optimal stimulation site for more permanent array positioning. Where the system is to be used to control heart rate and blood pressure, the mapping process may monitor for hemodynamic response indicating reduction in these parameters by a desired amount in response to stimulus.

Mapping preferably involves choosing the optimal array position, as well as choosing the combinations of electrodes to be energized and their polarities. Thus at each electrode array position to be explored during mapping, the electrodes may be energized in different combinations and with different polarities to discern which combination of vectors or polarities are best able to capture the target nerve and achieve the desired response. For example, possible vectors for the 4 electrode array might be left distal to right proximal, left distal to left proximal, left distal to right proximal, both left to both right, both proximal to both distal, etc.

As part of the mapping process, the user or the system might identify more than one beneficial combination of electrodes or vectors. Having more than one combination or vector identified allows the neuromodulation system to be programmed to change the electrode combination or vector so as to minimize the chance that the nervous system will adapt to the stimulus and diminish the effects of the stimulus. The system may be programmed to automatically change the electrode combination or vector periodically (e.g. every few days or few weeks), or in response to a diminution of stimulus effect by a predetermined amount or percentage.

Features of the first embodiment allow for repositioning of the electrodes during mapping to allow the optimal array position to be determined. In the first embodiment, a first temporary or mapping anchor 11 is positionable in contact with the vessel walls and the substrate 14 for use in retaining the electrodes at a chosen position during mapping. After mapping, a second anchor (described below) is used to chronically retain the electrodes at the selected position such that the electrodes remain at the target site identified during mapping.

The first anchor 11 biases the electrodes in contact with the vessel walls at the target site so as to ensure accurate mapping, but the radially outward forces imparted by the anchor against the surrounding vessel well are significantly lower than those imparted by the second anchor. The first anchor 11 may be releasably attached to the substrate 14, chronically attached to the substrate using an adhesive or molded onto the substrate, or it may be a separate component from the substrate.

Referring to FIG. 1A, the first anchor 11 may be formed of one or more loops 22 of resilient material including but not limited nitinol, stainless steel or resilient polymer. The loops 22 may be positioned on an elongate shaft 23. Each loop has a substrate contacting portion 24 and a vessel wall contacting portion 26 that extends away from the portion 24. In the illustrated example, the substrate contacting portion 24 of a loop 22 may be a u-shaped tip portion defined by generally parallel wire sections occupying a plane.

The vessel wall contacting portion 26 is shaped to contact the vessel wall at one or more points so as to bias the electrodes 12 against the vessel wall as shown in FIG. 1B. In the illustrated design, the wall contacting portion 26 defines a generally ovular shape and, as shown in the side section of FIG. 1B, extends proximally from the portion 24. Each of these features facilitates resheathing of the array, allowing it to be repositioned and then redeployed within the vessel for further mapping.

In this embodiment, the legs 23a of the wire forming the loop 22 extend proximally from the substrate and run adjacent (and preferably parallel) to one another near the point where they are connected to the shaft 23, allowing the legs to slightly cross one-another if the loop is deployed within a blood vessel having vessel diameter smaller than the fully expanded diameter of the loop 22. This ability of the legs to cross renders the loop 22 compatible with vessels having a greater range of diameters.

A mandrel 25 is detachably coupled to shaft 23. The mandrel 25 has a proximal portion that, in use, extends outside the body so that the mandrel may be manipulated by the user to assist in positioning the first anchor 11 and the substrate 14 within the vasculature.

Although FIG. 1A shows narrow portion 16 of the substrate 14 spaced from elongate shaft 23 and mandrel 25, it might instead be routed along the proximal-most anchor loop 22 and elongate shaft 23, allowing the lead 17 to extend adjacent to mandrel 25 as shown in FIG. 1B.

Figure 2A:
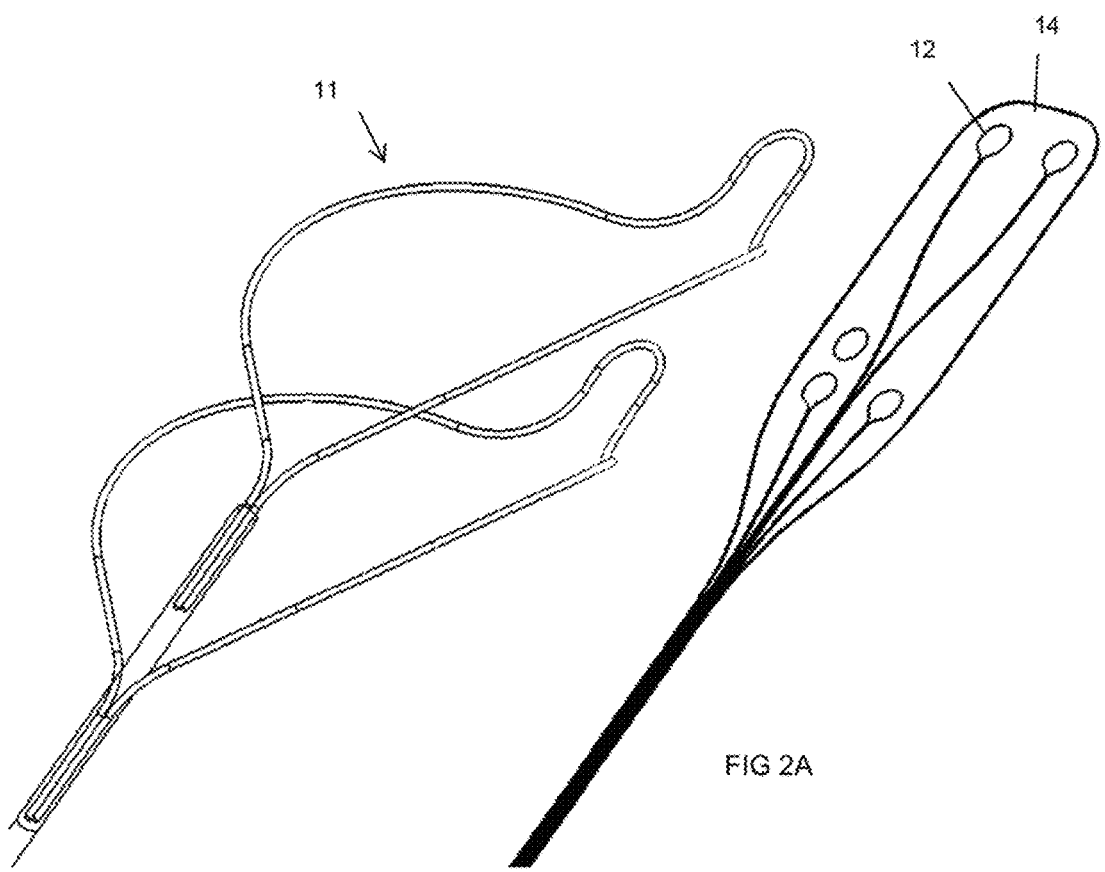
FIG. 2A is similar to FIG. 1A but shows the anchor and array separated from one another.
Figure 2B:
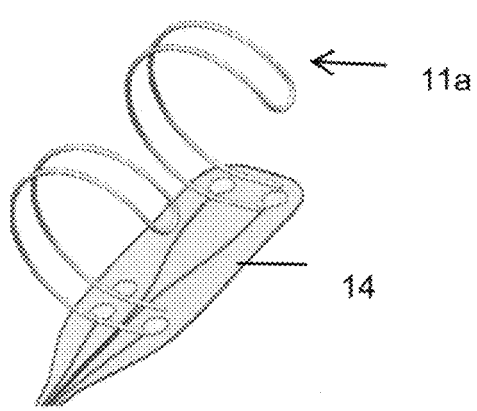
FIGS. 2B-2D show the array of FIG. 2A with alternate temporary anchor designs.
Figure 2D:
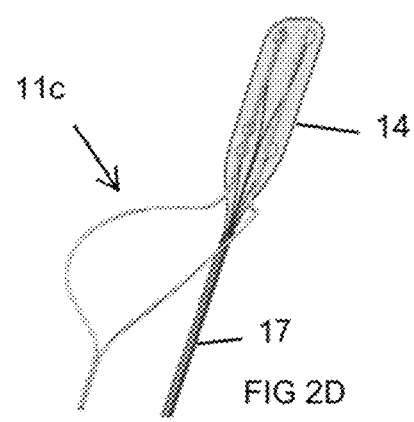
Figure 2C:
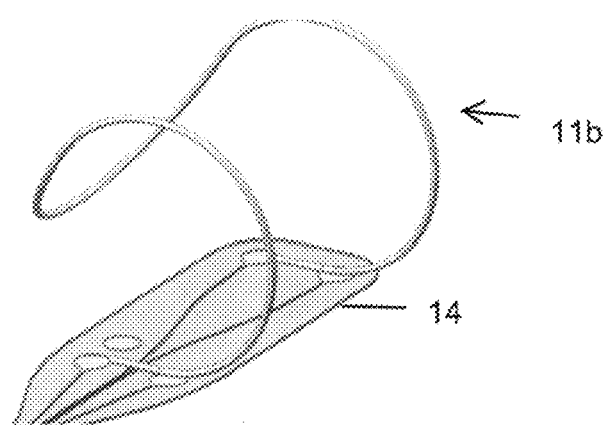

Other first anchor shapes include, but are not limited to, those shown in FIGS. 2B-2D. In the FIG. 2B embodiment, two anchors 11a are shown, each of which comprises a length of wire formed into a "U" shaped element. The wire ends forming the legs of the "U" are coupled to the substrate 14, spaced from one another (and from the other anchor) in a longitudinal direction relative to the substrate. The curved base of the "U" forms a free end of the anchor. The portion of each anchor extending from the legs to the base of the U curves around the longitudinal axis of the substrate so as to allow the anchor to circumferentially contact the vessel wall when deployed. Is this embodiment, the positioning mandrel (not shown) is detachably coupled to either or both of the anchors or to the substrate.

The FIG. 2C anchor 11b is similar to that of FIG. 2B but uses a single wire positioned with the legs of the "U" further apart along the longitudinal length of the substrate 14.

The FIG. 2D anchor 11c is similar to that of FIG. 2A, but uses a single anchor loop.

Figure 3:
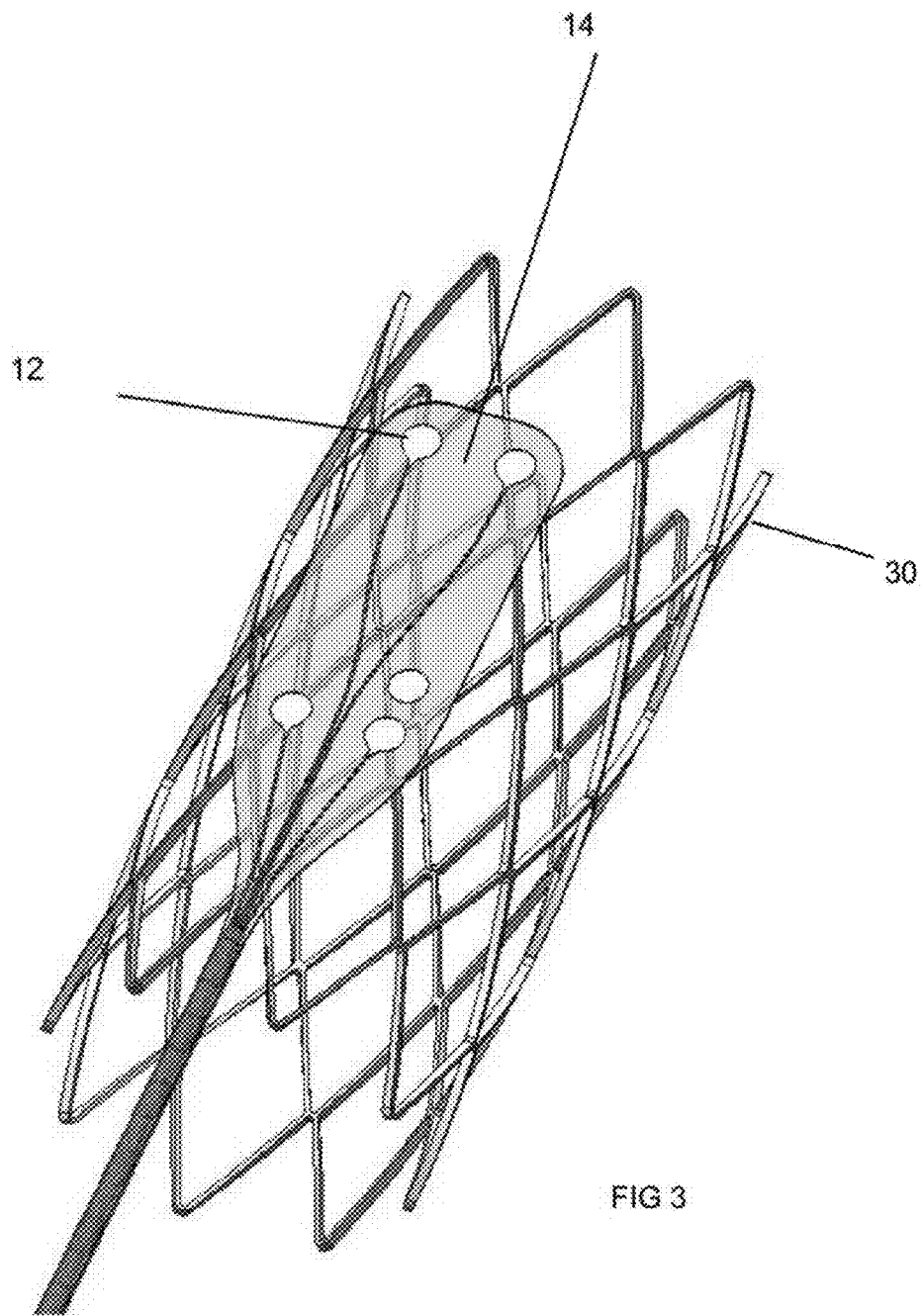
FIG. 3 is a perspective view showing the FIG. 1A electrode array and the chronic anchor arranged with the vessel-wall contacting surface of the substrate facing upwardly, and with the opposite surface of the substrate in contact with the anchor.

The FIG. 1-2C embodiments are preferably part of system that additionally includes a second anchor for more permanently anchoring the array within the blood vessel once the optimal electrode position has been selected. As shown in FIG. 3, the second anchor 30 may be an expandable sleeve or stent-like device formed of nitinol, stainless steel, or other resilient material known for use in manufacturing stents. Second anchor 30 is configured to be advanced from a catheter 27 passed through the loops 22 of the temporary anchor as indicated by the arrow in FIG. 1B. The second anchor expands as it is advanced from the catheter 27, thus sandwiching the electrode array between the anchor 30 and the vessel wall.

Deployment of the electrode and anchor system according to the first embodiment will next be described.

Prior to use, the positioning mandrel 25 is coupled to the temporary anchor 11 and the array and temporary anchor are disposed within a delivery sheath (not shown). The sheath is percutaneously introduced into the vasculature using known methods, and then advanced to a desired location with a target vessel (e.g. the superior vena cava or internal jugular vein for vagus nerve stimulation). The substrate 14 and first anchor 11 are released from the sheath, such as by withdrawing the sheath while maintaining the position of the anchor using the mandrel 25. The temporary anchor expands in the vessel and thus retains and biases the electrodes 12 in contact with the vessel wall as shown in FIG. 1B. Mapping is performed by releasing and engaging the electrode against the vessel wall in this manner, then stimulating and observing/monitoring the response. If additional mapping is deemed necessary, the procedure also includes recovering the array and anchor into the sheath by advancing the sheath distally while maintaining counter-traction on the mandrel. The sheath is advanced to another location and the process is repeated until the target location (at which the most optimal response to stimulation is measured) is identified.

Once the target location is identified, the catheter 27 carrying the second anchor 30 is passed through the loops 22 of the temporary anchor as indicated in FIG. 1B. The second anchor is released from the catheter 27 using methods known to those skilled in the art. The second anchor expands into contact with the inwardly-facing surface (relative to the vessel wall) of the substrate as shown in FIG. 3. The expanding anchor 30 sandwiches at least a portion of the substrate 14 between the anchor 30 and the vessel wall so as to chronically bias and retain the electrodes 12 against the wall. Because the anchor 30 is expanded from within the loops 22 of the first anchor 11, at least a portion of the first anchor 11 is also captured between the anchor 30 and the vessel wall or substrate. The mandrel 25 is detached from the first anchor 11 and is withdrawn from the body. The lead 17 may be attached to a pulse generator before or after placement of the system 10. In one embodiment, the lead 17 is coupled to a fully intravascular pulse generator, such as is described in the aforementioned prior applications. Where the electrode array is to be deployed in the superior vena cava or internal jugular vein, the pulse generator may be deployed in the inferior vena cava, the superior vena cava, or elsewhere in the vasculature, subcutaneously, or outside the body.

Second Embodiment

Figure 4A:
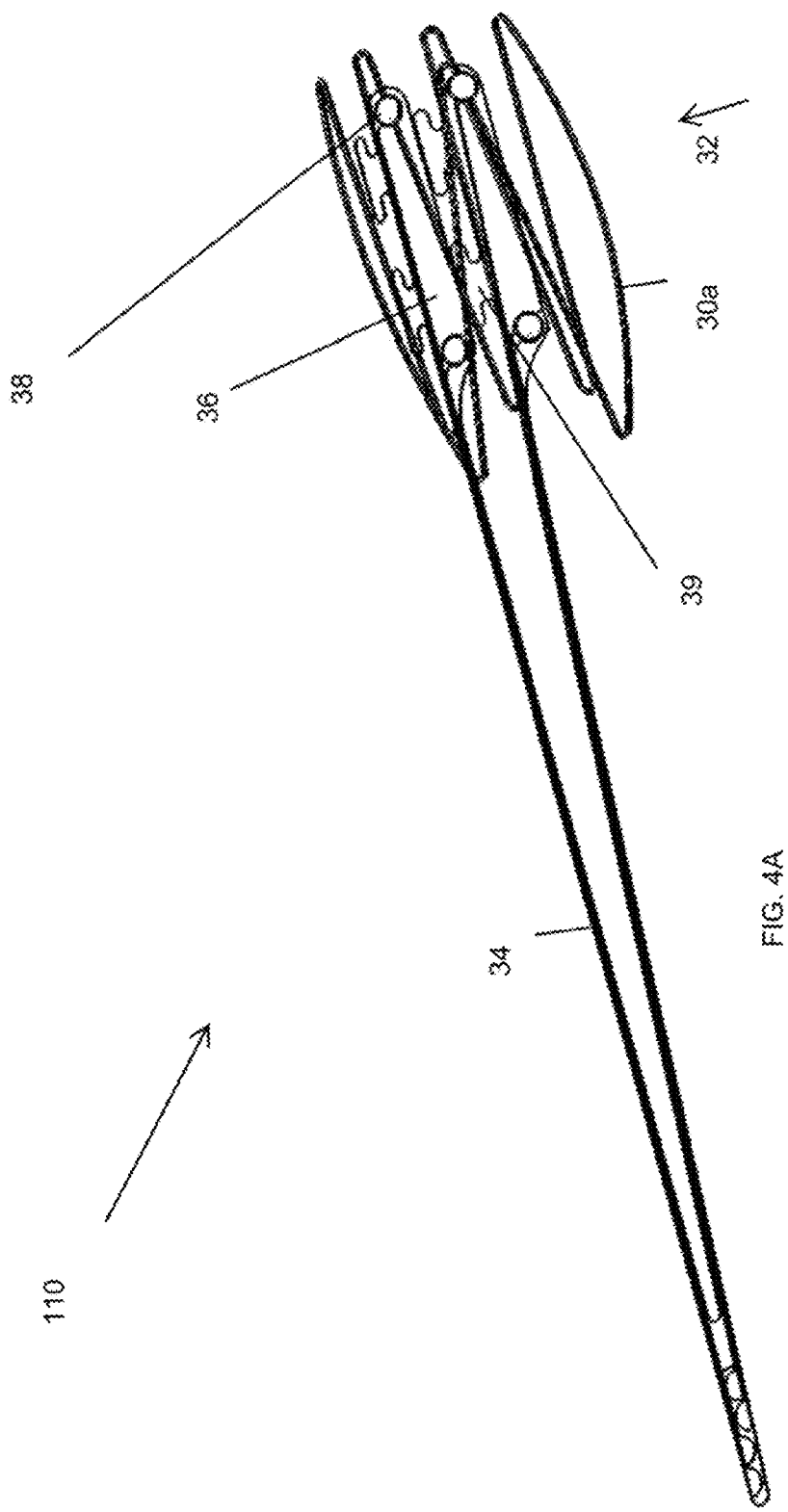
FIGS. 4A and 4B are perspective views of a second embodiment of an array and anchor.
Figure 4B:
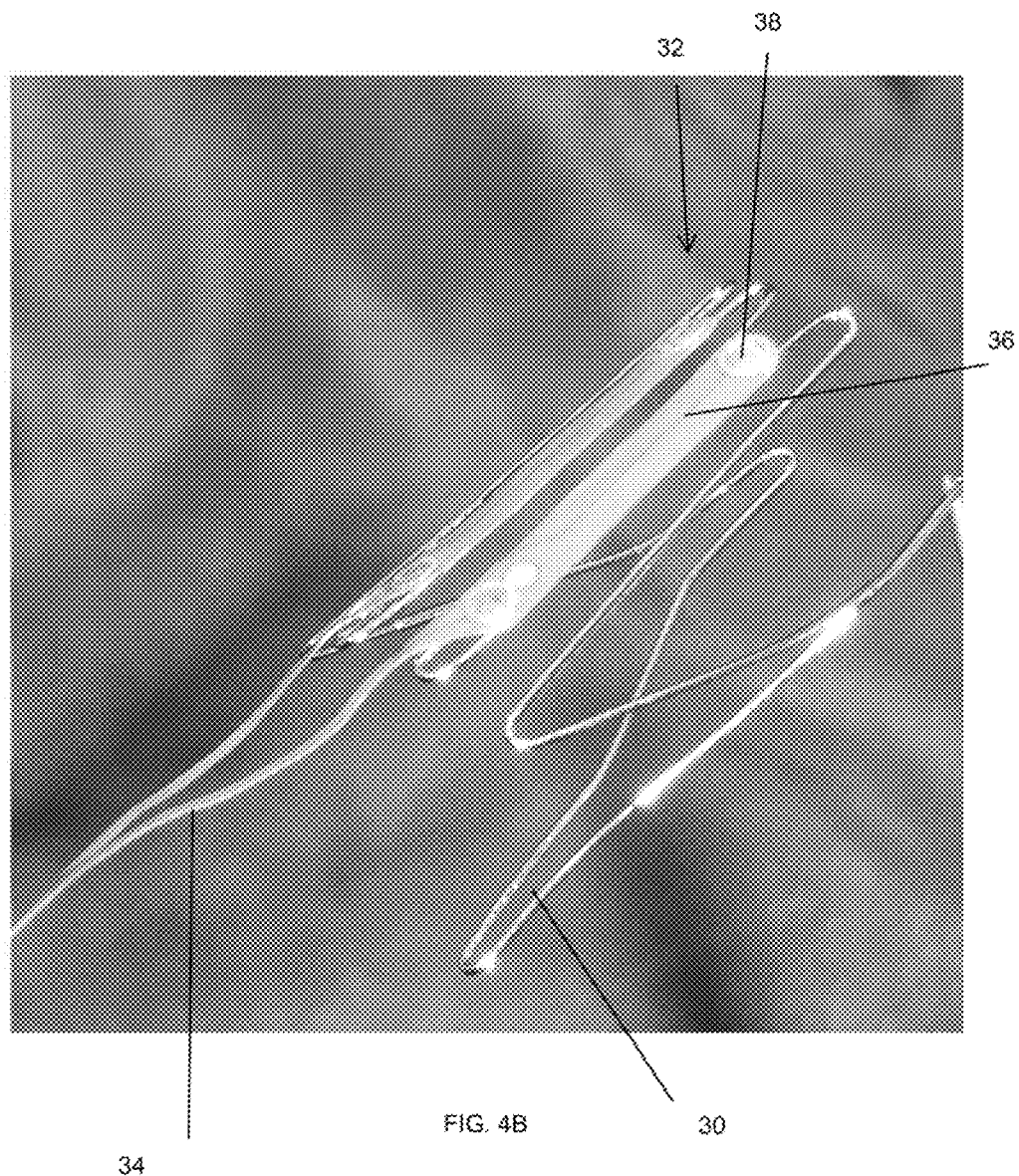

A second electrode array and anchor system 110 is shown in FIGS. 4A and 4B. The second system utilizes a self-expanding anchor 30a in combination with a flexible electrode array 32, which may be attached to the anchor or which may simply be positioned in contact with the anchor. In one form of this embodiment, the anchor 30a is attached to the array 32 and is employed to bias the electrodes against the vessel for mapping as well as for chronically retaining the array within the vessel. The array includes two or more flexible, longitudinal, splines 34, each supporting a flexible circuit member or arm 36. Materials suitable for use in manufacturing the second embodiment include those listed for use with the first embodiment. For example, the members 36, and optionally the splines 34, may be formed of flexible substrate materials of the type disclosed above in connection with the first embodiment of FIG. 1A. In one embodiment, the splines and the members are integral components of a single flexible substrate.

Two or more electrodes 38 are longitudinally arranged on each member 36, and aligned or offset from one another as described with respect to the first embodiment. As with the first embodiment, conductors or conductive traces are formed on or molded into the substrate and extend proximally from each of the electrodes, terminating at contacts near the proximal ends of the splines. A lead (not shown) which may be formed of tubing, shrink material, or other suitable material, is disposed over at least a proximal portion of the array (such as the portion of the substrate where the splines 34 meet at the proximal end), and includes conductors electrically coupled to the contacts of the array's conductors or traces.

Figure 5:
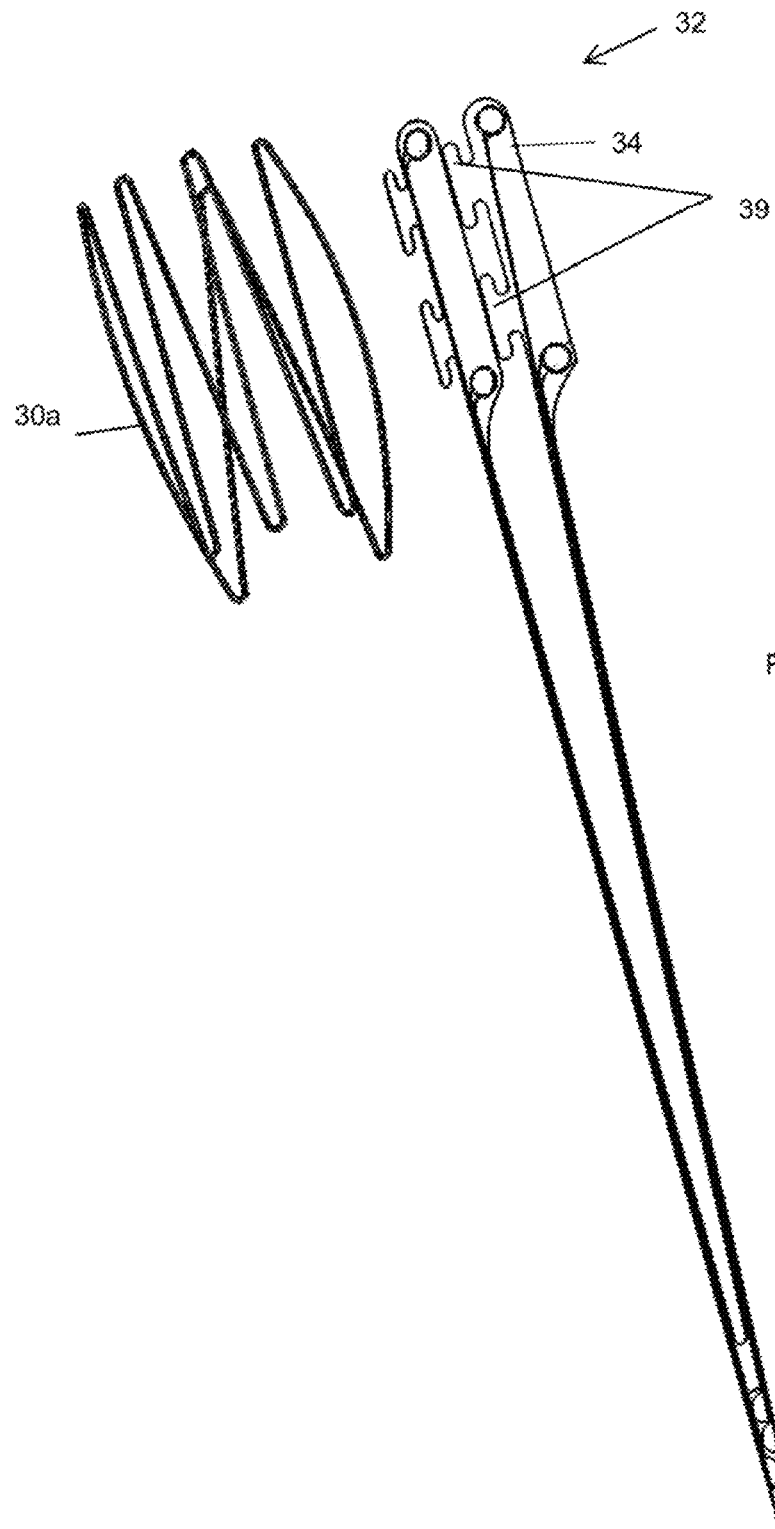
FIG. 5 is an exploded view of the system of FIG. 4A.
Figure 6:
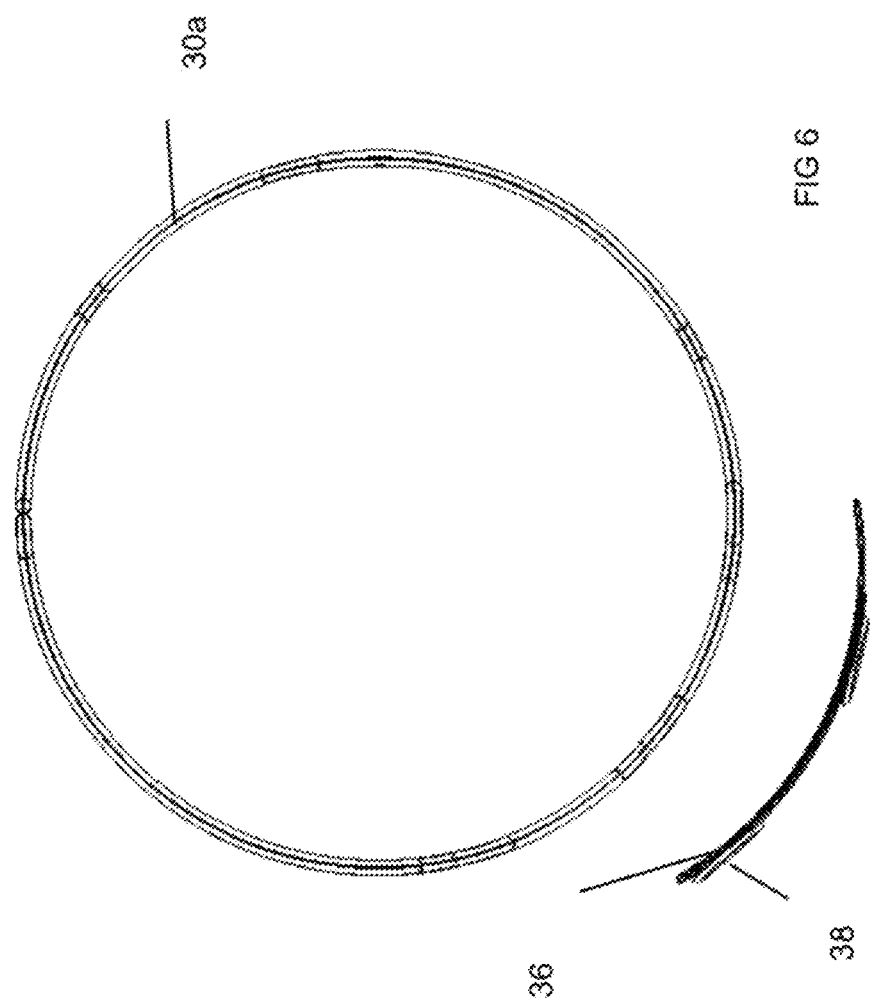
FIG. 6 is a distal end view of the system of FIG. 4A, with the anchor exploded from the substrate.

The flexible substrate material of the array 32 may include a plurality of tabs 39 on members 34. The tabs are most easily seen in FIG. 5. During manufacture, tabs 39 are folded around struts of the anchor 30a and secured using an adhesive and/or a coating (e.g. polyurethane or silicone) applied to the substrate and its tabs. Other techniques for securing the tabs in the folded position include ultrasonic welding or focal heating of the folded tabs to cause opposed sections of the polymer to melt together. FIG. 4A shows the assembly before the tabs 39 have been folded over the struts of the anchor 30a. FIG. 4B shows the assembly after the tabs have been folded. When the system is assembled, the electrodes 38 are positioned such that their conductive surfaces face away from the anchor 30a and will contact the inner wall of the target vessel when the anchor 30a is expanded, See FIG. 6.

The array and anchor system is deployable from a sheath as discussed above. The delivery system used to deploy the array and anchor from the sheath may include a mechanism for maintaining engagement between the delivery system and the anchor 30a during mapping, so that the anchor 30a and array 32 may be resheathed and/or repositioned during the mapping procedure.

Figure 7:
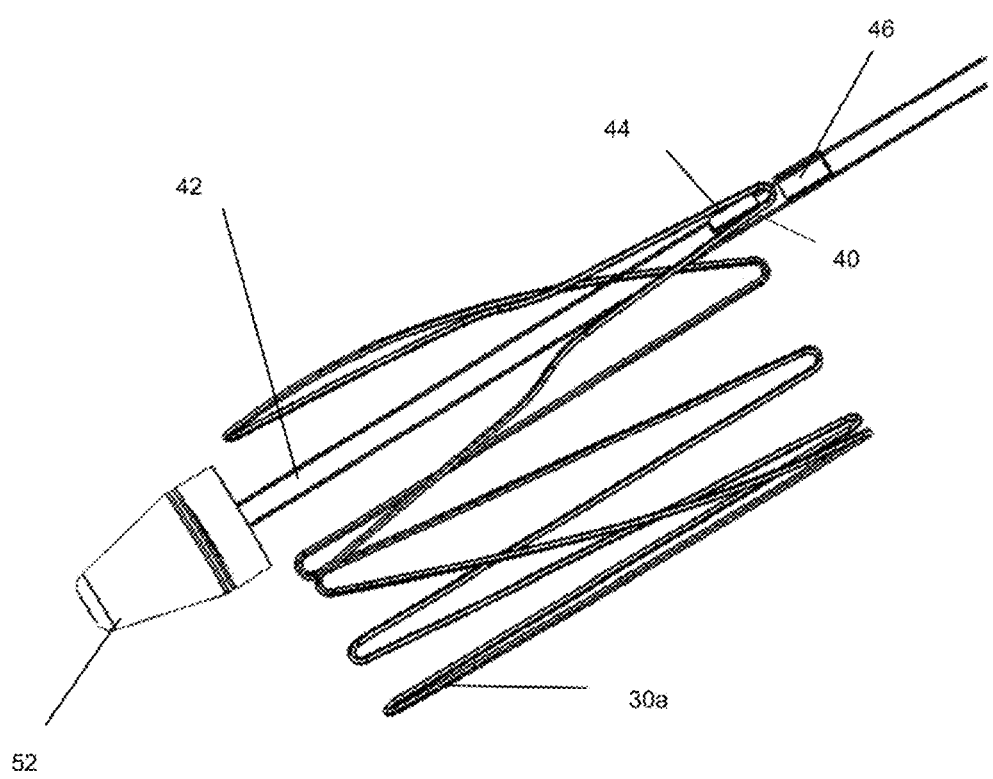
FIG. 7 shows the anchor of FIG. 4A mounted to a delivery mandrel. The substrate and electrodes are not shown for purposes of clarity.
Figure 8:
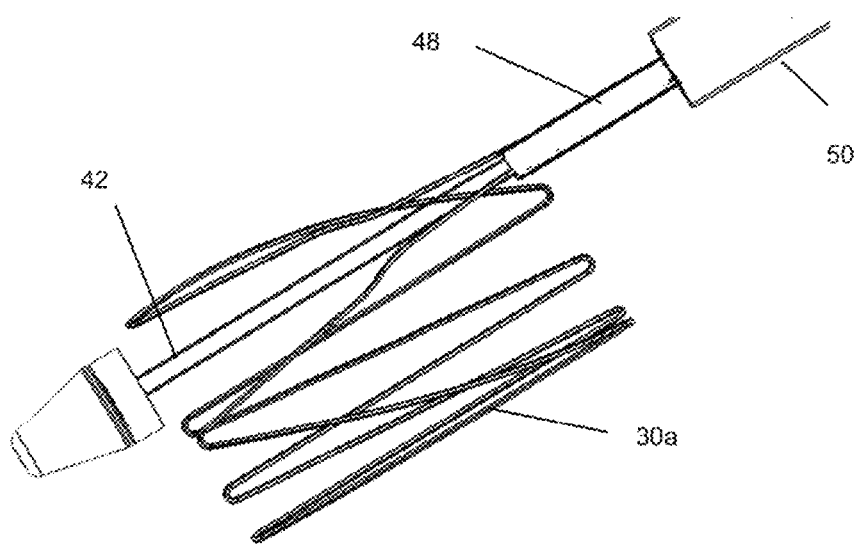
FIG. 8 is similar to FIG. 7 and further shows a portion of the anchor retained on the mandrel by the inner sheath.

For example, referring to FIG. 7, in which the substrate is not shown for purposes of clarity, anchor 30a may include a u-shaped spline 40 that extends further proximal than the remainder of the anchor 30a. A shaft 42 for carrying the array/anchor assembly during deployment includes a distal stop 44 and a member 46. Anchor 30a is coupled to the delivery system by positioning a portion of spline 40 (such as the U-bend at the proximal end) between the stop 44 and member 46. The spline 40 is captured in this position using an inner sheath 48 (FIG. 8) that is slidable distally over the shaft 42. In this position, the sheath 48 is disposed over the stop 44 and member 46 to retain the spline 40 between them. With the spline captured, the anchor 30a may be compressed within an outer sheath 50, which is slidably positioned over inner sheath 48 as shown in FIG. 9.

The shaft 42 has a longitudinal axis that may be parallel to but laterally offset from the longitudinal axis of the sheath 50. This arrangement may be used to allow additional room for the compressed anchor and the substrate/electrodes between the shaft and the adjacent inner wall of the sheath's lumen.

The distal end of the shaft 42 may include an atraumatic tip 52 as shown in FIG. 7. The tip 52 may include a hole or annular groove on its proximally-facing end for receiving the distal end of the outer sheath 50 (FIG. 9) and a throughbore (not shown) within which the distal end of shaft 42 is seated. This arrangement provides a smooth transition between the distal end of the outer sheath 50 and the tip 52.

Figure 9:
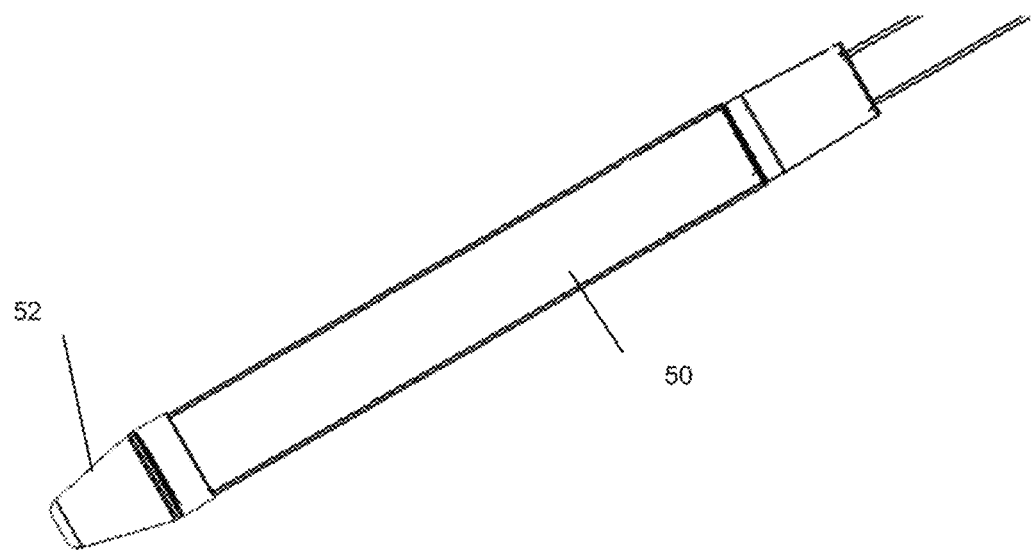
FIG. 9 is similar to FIG. 8, but the anchor is compressed within the outer sheath.
Figure 10:
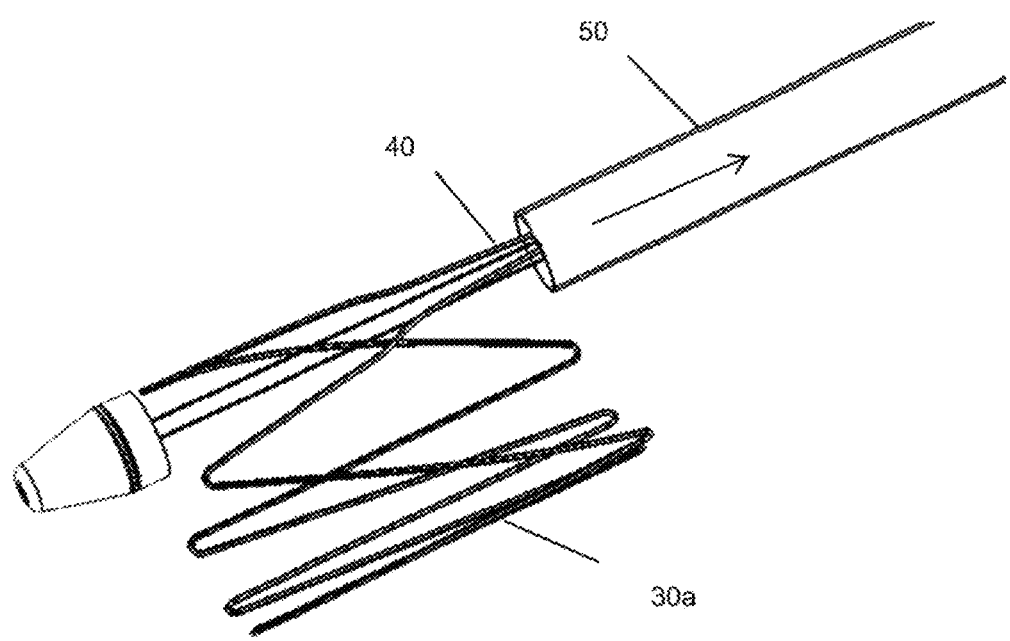
FIG. 10 is similar to FIG. 9 but illustrates withdrawal of the outer sheath to allow expansion of the anchor.

Prior to deployment of the array and anchor system of the second embodiment, the components are arranged as shown in FIG. 9. The system is percutaneously introduced and advanced to the target vessel, and then positioned at the predicted target location. In this step, the system may be advanced over a guidewire extending through shaft 42 and tip 52. Outer sheath 50 is withdrawn as indicated by the arrow in FIG. 10, to release the anchor 30a from the outer sheath 50. The anchor expands, positioning the electrodes in contact with the surrounding walls of the blood vessel at the predicted target location. The inner sheath 48 remains positioned as in FIG. 8 so the anchor 30a stays coupled to the shaft 42. Note again that in FIGS. 7-10 the substrate and electrodes are not shown to allow the remaining components to be more easily seen.

The electrodes are activated at the predicted target location and the response is measured (for example, where the target nerve is the vagus nerve, heart rate and/or blood pressure response to the stimulus may be monitored). If the user wishes to test a different electrode position, the shaft 42 is manipulated to change the position of the electrodes within the vessel. For example, shaft 42 may be rotated to move the electrodes to a different rotational position along the blood vessel wall, and/or it may be linearly advanced or retracted to move the electrodes distally or proximally in the vessel.

To facilitate repositioning, inner shaft 48 (FIG. 8) is moved further distally over spline 40. Given the v-shape of the spline 40, this distal movement folds the legs of the "v" towards one another, and in doing so radially collapses the anchor 30*a*, reducing its diameter. (In a variation of this embodiment, a tether coupled to the apex of spline 40 might be instead be withdrawn to similarly collapse the anchor.) In some embodiments, the sheath may be moved over the collapsed anchor to further collapse and/or enclose the anchor for repositioning. In other embodiments, the anchor is not resheathed prior to repositioning. In either case, the radially collapsed anchor is repositioned and then redeployed by retracting the inner shaft 48 to allow the anchor to expand.

Once the array is repositioned, the electrodes are again activated and the response is measured in the second position. The process is repeated until an optimal electrode site is determined. Once the electrodes are determined to be at the optimal site, the inner sheath 48 is fully withdrawn from the anchor, allowing the shaft 42 to be detached from the spline 40 of anchor 30*a*. The shaft 42 and sheaths are removed from the body, leaving the anchor 30*a* and substrate 34 in the selected position in the blood vessel, with the electrodes remaining at the determined optimal site.

Third Embodiment

FIGS. 11A through 12B illustrate an alternative array and system 210. The system of the third embodiment includes an anchor 30*b* in which temporary and chronic anchoring capabilities are integrated into a single structure. The anchor includes first and second portions. The first portion has radial expansion forces that will retain the electrodes against the vessel wall for mapping, allowing the optimal electrode site to be determined. The second portion has greater radial expansion forces so as to chronically retain the implant at the chosen position within the vessel once the optimal electrode site has been selected.

In a preferred embodiment, the anchor is an expandable stent-like sleeve. The first anchor portion 56 is preferably positioned distally of the second anchor portion 58. During use, the first portion 56 is first deployed to hold the electrodes 12 sufficiently in contact with the vessel wall to ensure electrical contact for mapping, but using light enough radial expansion forces to allow for repositioning and/or re-sheathing of the electrodes as needed during a mapping procedure. Second portion 58 of the anchor is deployed after mapping has been completed and the electrodes are in the determined optimal position. It functions to firmly and chronically retain the electrodes at the chosen position. In a preferred anchor, the second portion 58 possesses radial forces sufficient to outwardly distend the vessel wall when it is deployed in the vessel, whereas the first portion 56 will not outwardly distend the vessel wall.

Anchor 30*b* is preferably formed of a length of tubing of resilient material such as nitinol that is laser cut to the desired pattern and shape set in its expanded shape. The patterns of the struts forming first and second portions 56, 58 may take a variety of different forms. In the illustrated embodiment, second portion 58 includes a single circumferential ring in which the struts 60 form generally diamond-shaped openings. These openings are arranged with two opposed corners 62*a, b* (FIG. 11A) of the diamonds extending longitudinally in distal and proximal directions, and the other two opposed corners 64 extending circumferentially. In a preferred embodiment, the angles between the struts 60 at the corners 62*a*, 62*b* are approximately 45 degrees or less.

Figure 12A:
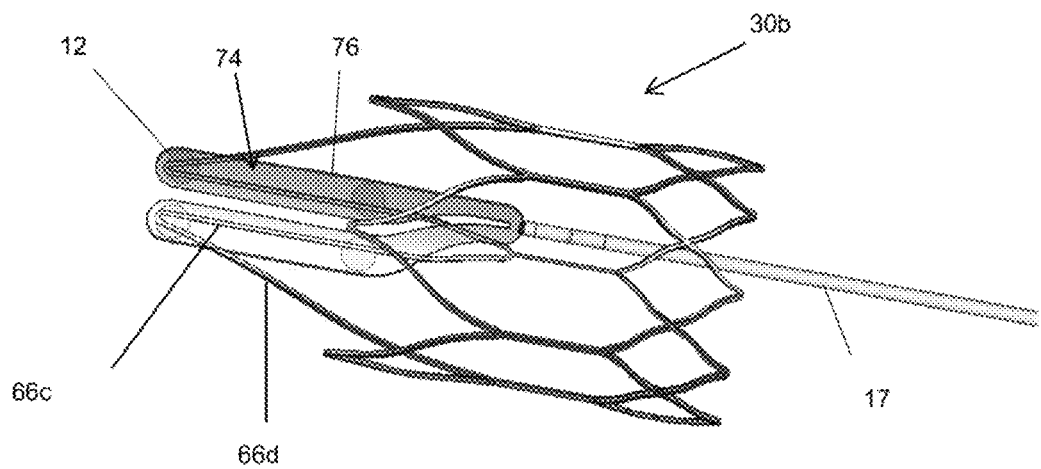
FIG. 12A is a perspective view of the electrode and anchor of FIG. 11A.
Figure 12B:
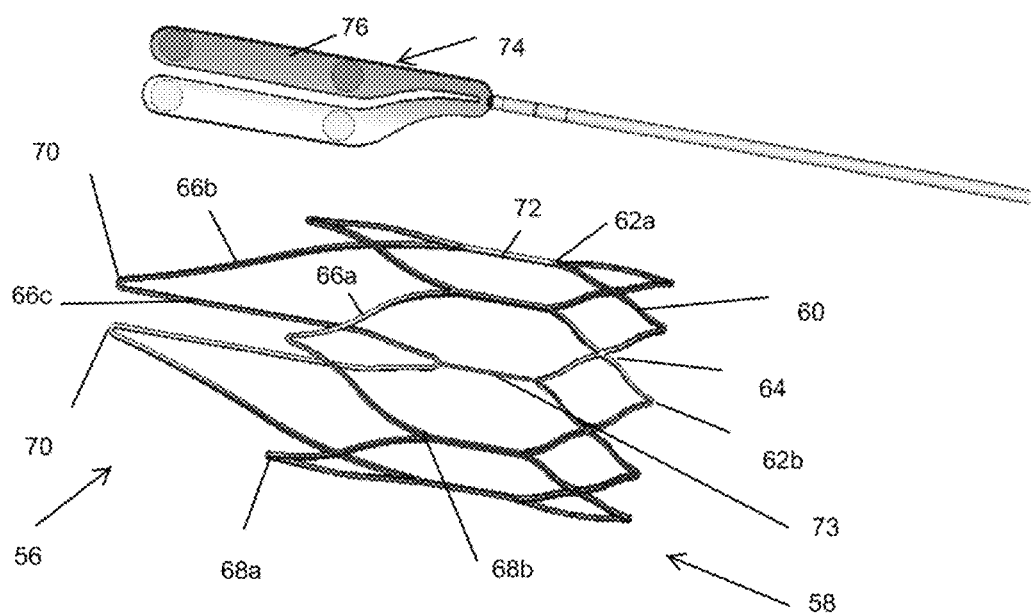
FIG. 12B is similar to FIG. 12A and shows the anchor exploded from the substrate.

Referring to FIG. 12B, the struts forming the first portion 56 of the illustrated embodiment includes struts 66*a-c* formed in an open, undulating pattern with distal peaks 68*a*, 70 and proximal peaks 68*b*. The struts 66*a-c* have a length that is longer than that of the struts 60 forming the diamond pattern of the second portion 58.

Two of the distal peaks 70 extend further distally than the other distal peaks 68*a*. The struts 66*b*, 66*c* forming these peaks 70 support the electrodes 12 as will be discussed below. Peaks 68*b* are preferably aligned with one another around the circumference of the anchor.

Each of the proximal peaks 68*b* is connected by a longitudinal strut 72, 73 to a longitudinally aligned distal corner 62*a* of the second portion 58. The longitudinal struts 72, 73 are preferably equal in length. An alternative embodiment eliminates the longitudinal strut 73 extending from the proximal ends of struts 66*c* for reasons that are discussed below.

The design of the anchor 30*b* results in a first section 56 that exerts smaller radial forces against the vessel wall than the second section 58 and that is more compressible in a radially inward direction than the second section. These different characteristics result from the fact that the first portion 56 uses struts 66*a-c* that are longer than those 60 of the second section—placing longer lever arms relative to the fold points 68*a*, 68*b* in the first portion than those 62*a*, 62*b*, 64 in the second portion. Moreover, the first portion possess fewer such fold points than the second portion, making it less able to resist compression in response to radially inward forces imparted by the vessel wall.

Electrode arrays of the type disclosed herein, or alternative forms of electrodes, are mounted to or formed on the anchor so as to contact the surrounding vessel wall when the anchor is expanded. Referring to FIGS. 12A and 12B, in the embodiment as shown, electrodes 12 and associated conductors (not shown) are formed on or molded into a flex circuit substrate 74 having a pair of parallel strips or members 76 on the distal end of lead 17. Strips 76 may be asymmetrically or symmetrically arranged. The lead 17 may be laterally offset from the longitudinal axis extending between and parallel to the strips 76 as shown, or it may extend along the longitudinal axis. The substrate preferably has properties similar to those disclosed above with respect to the first and second embodiments. Each strip includes at least one distal and one proximal electrode 12 longitudinally aligned with one another. A larger number and/or different arrangement of electrodes may be used as discussed above.

Referring to FIG. 12A, the substrates 74 are mounted to or molded onto struts 66*b*, 66*c*. The electrodes 12 on the strips 76 are distal to the cross-sectional plane defined by peaks 68*b* (in other words, distal to the struts 72, 73). Struts 66*b*, 66*c* will preferably maintain the longitudinal alignment of the electrodes on the strips 76. In the illustrated embodiment, each strut 66*c* angles outwardly from longitudinal strut 73 and from there extends parallel to the longitudinal axis of the anchor—causing the electrode carrying distal portions of the struts 66*c* to extend in parallel to one another. In other embodiments, an additional strut or arrangement of struts may extend between two struts 66c to maintain separation between them and preferably to keep them parallel to each other.

Figure 13:
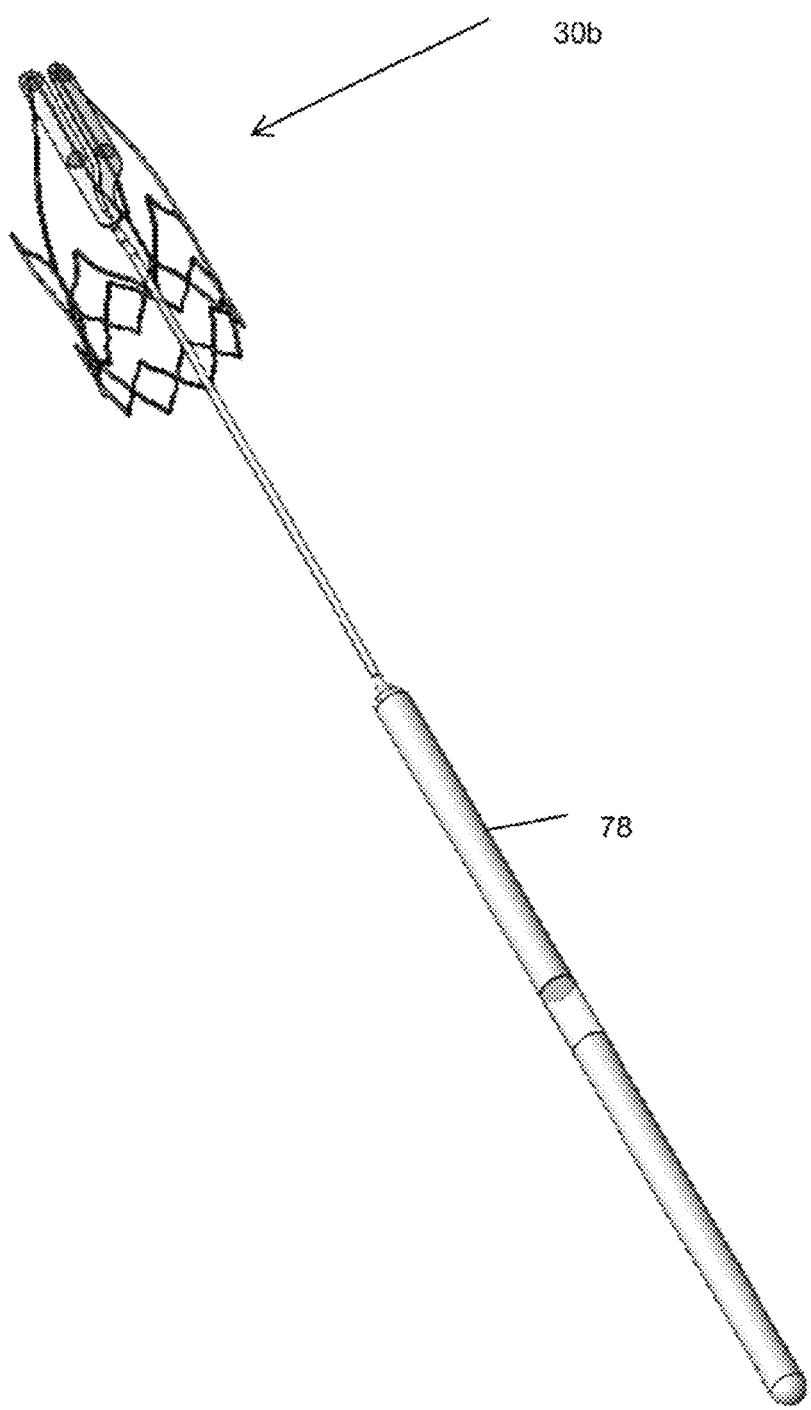
FIG. 13 illustrates the electrode and anchor of FIG. 11A coupled to an intravascular implant.

As shown in FIG. 13, the anchor and array system of the third embodiment may be used in a fully intravascular system having an intravascular housing 78 containing a pulse generator, battery, and related circuitry and electronics. In other designs, lead 17 may be coupled to a subcutaneous pulse generator. In still other arrangements, the anchor and array system may be in wireless communication with a pulse generator implanted within the vasculature or the subcutaneous space, or located outside the body, eliminating the need for the lead 17.

Figure 14B:
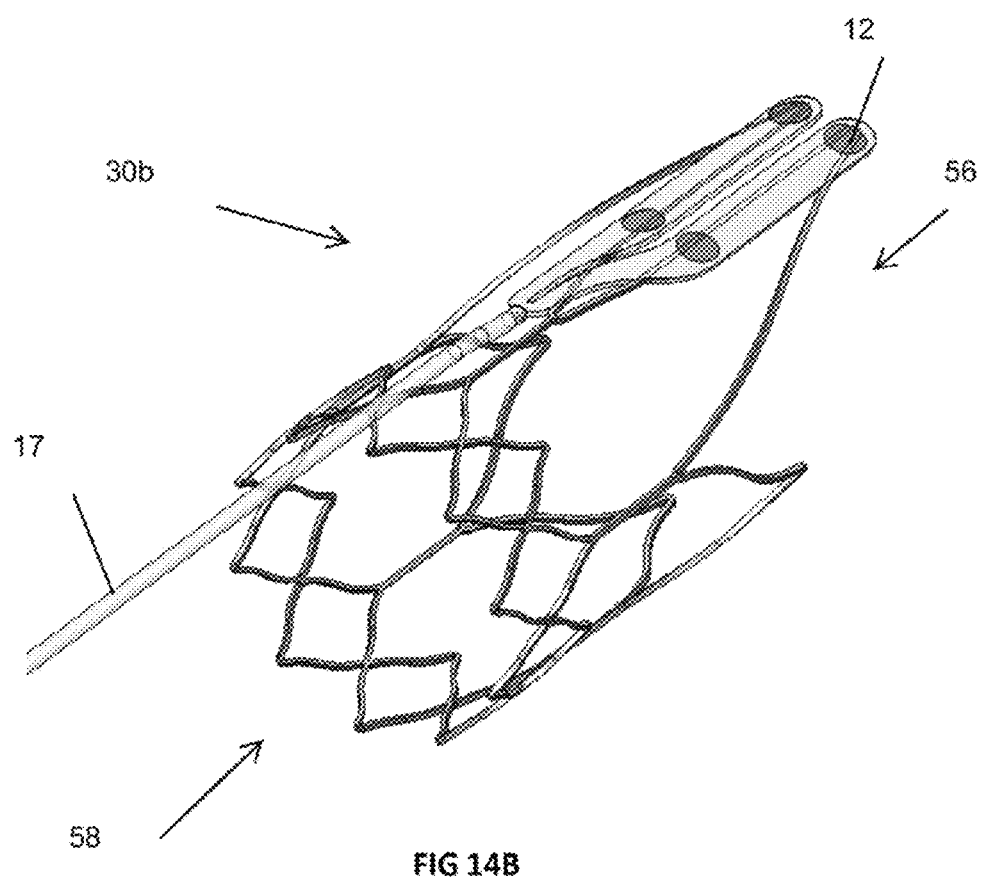
FIG. 14B is a perspective view of the anchor and electrodes of FIG. 11A with the second portion of the anchor deployed for chronic retention of the electrodes within the vasculature.

FIGS. 14C and 14D illustrate components of a delivery system that may be used to deploy the electrode system. In use, the integrated anchor (not shown in FIG. 14C) is disposed within a delivery sheath 50 prior to delivery into the vasculature. A tubular shaft 51 extends through the sheath 50. A member 53 carried by the shaft 51 is coupled to or in contact with the proximal portion of anchor. Member 53 aids deployment by providing counter-traction during movement of the sheath 50 relative to the anchor (for deployment and for resheathing when necessary). Member 53 is proportioned to allow the lead 17 to pass between the member 53 and the adjacent wall of the sheath's lumen as shown in FIG. 14D. In the illustrated embodiment, the member 53 has a generally circular cross-section except for a beveled face 55 that provides this clearance for the lead 17.

A small diameter flexible tube 82 slidably extends through the tubular shaft 51 and includes a tip 52 similar to the tip described above with respect to the second embodiment. A guidewire lumen extends through the tube 82 and a corresponding throughhole passes through the tip 52, allowing the assembled sheath 50, anchor, tubular shaft 51 and small diameter tube 82 to be advanced through the vasculature over a guidewire. As best shown in FIG. 14D, the longitudinal axis L of the shaft 51 and flexible guidewire tube 82 are laterally offset from the longitudinal axis C of the sheath 50 so as to provide space for the anchor and substrate between the guidewire tube 82 and the inner wall of the sheath 50. When assembled for delivery, the outer appearance of the system may be similar to that shown in FIG. 9, with the sheath 50 and tip 52 forming an atraumatic outer assembly for smooth delivery through the vasculature.

The assembled delivery system, anchor and array is percutaneously introduced and advanced to a desired location with a target vessel (e.g. the superior vena cava or internal jugular vein for vagus nerve stimulation). The sheath 50 is partially withdrawn while the member 53 holds the longitudinal position of the anchor 30b within the vessel. The sheath is withdrawn until the first portion 56 of the anchor 30b is released from the sheath 50 as shown in FIG. 14A, placing and biasing the electrodes 12 into contact with the vessel wall. If needed, distally-directed pressure is applied to the lead 17 so as to avoid the potential that excess tension on the lead might prevent the electrodes from fully contacting the vessel wall. When the anchor is in the mapping position shown in FIG. 14A, the first portion 56 is external to the sheath 50 and in the expanded position. At least a portion of the struts 72, 73 connecting the first and second portions 56, 58 may also be disposed outside the sheath 50, while the second portion 58 remains compressed inside the sheath 50

With the anchor in the mapping position, mapping is performed at the target location. The properties of the first portion 56 allow it to be resheathed by advancing the sheath 50 over first portion 56 while providing counter-traction using the lead 17. The anchor 30b is then repositioned and redeployed so that mapping may be carried out at additional sites if necessary. Once the optimal stimulation site is determined, the position of first portion 56 within the vessel is maintained and the first portion remains expanded, keeping the electrodes against the vessel wall at the determined optimal location. The sheath 50 is fully withdrawn to release the second portion 58 of the anchor to the position shown in FIG. 14B. The second portion 58 expands against the vessel wall, thus firmly anchoring the electrodes at the chosen location within the blood vessel. The deployed second portion will preferably impart forces against the vessel wall that will cause the adjacent vessel wall to expand. Note that because the electrodes are positioned distal to the second portion 58 of the anchor, expansion of the vessel surrounding the second portion will not appreciably displace the electrodes from their position.

It is highly desirable during mapping to ensure that the electrodes fully contact the vessel walls. In a variation of the third embodiment, the strut 73 (FIG. 12B) disposed between the longer distal peaks 70 is eliminated. Thus the proximally extending peak formed by struts 66c, 66c is not restrained by such a longitudinal strut. By forming this peak to be free from longitudinal restraints at its proximal end, the full lengths of the struts 66c (and the electrodes they carry) are free to move into contact with the vessel wall when the first portion 56 is expanded and the second portion remains compressed. Other embodiments shown in FIGS. 15 through 17B use alternate configurations to ensure contact between the electrodes and the vessel wall during mapping and full deployment.

Figure 11A:
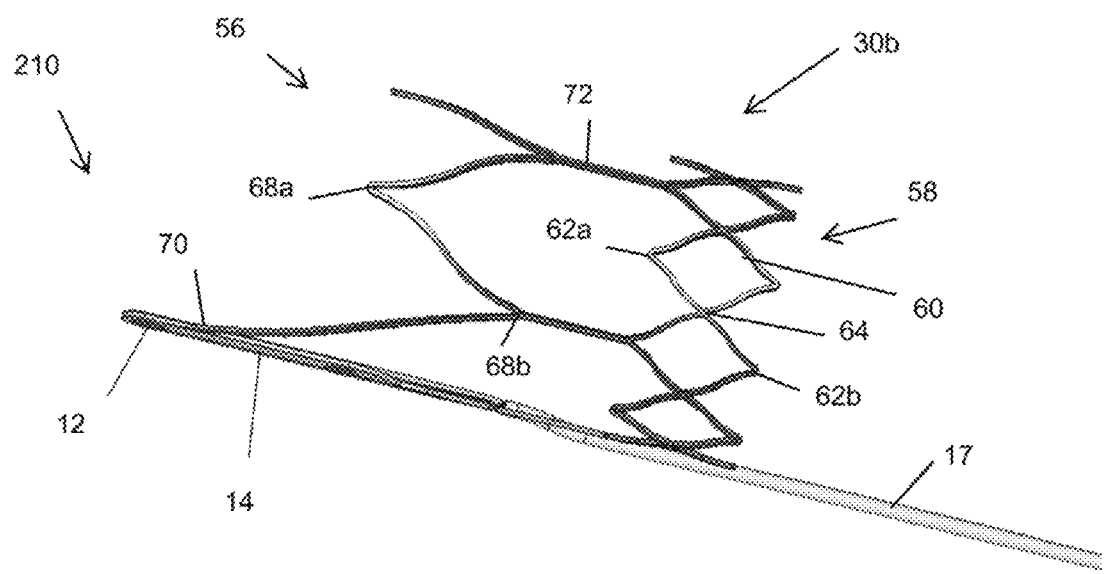
FIG. 11A is a side elevation view of an alternative electrode and anchor configuration.
Figure 11B:
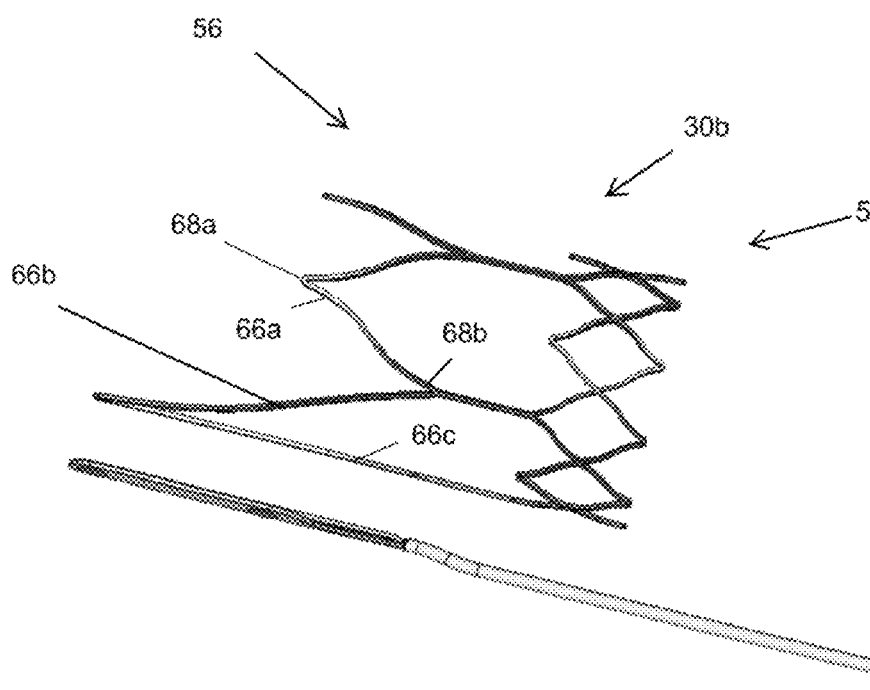
FIG. 11B is similar to FIG. 11A and shows the anchor separated from the substrate.
Figure 15:
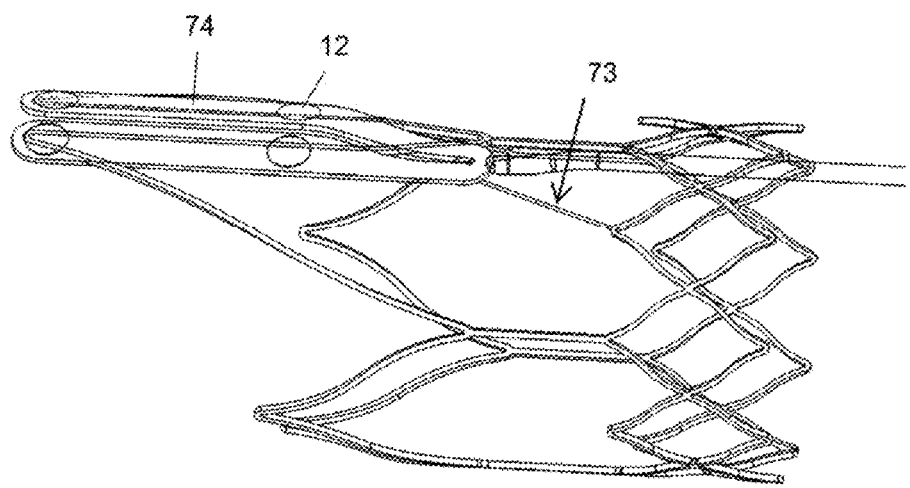
FIG. 15 is a perspective view of a variation of the anchor and electrodes of FIG. 11A.

In particular, the FIG. 15 embodiment differs from the FIG. 11A embodiment in that strut 73 is shape set to extend away from the longitudinal axis of the anchor, so as to outwardly bias the proximal portions of substrate 74 (and thus the electrodes 12). In the FIG. 16A, 16B embodiment, strut 73 is replaced by an expansion feature 73a biased such that when it is deployed from the sheath, its elements 76, 78, 80 unfold to bias the substrate towards the vessel wall. Rather than being a single strut connecting first and second portions of the anchor, expansion feature 73a has a distal end in the form of a strut 76 connected to the apex between struts 66c. Proximal end of strut 76 is connected to the cross-piece of a first U-shaped portion 78 which nested within a second U-shaped portion 80. The base of second U-shaped portion is coupled to a corner 62a of the second portion 58 of the anchor. Each U-shaped portion 78, 80 has a leg connected at its distal end to the corresponding leg of the other U-shaped portion. When the first portion 56 is expanded, expansion feature 73a unfolds to place strut 76 generally in parallel to the longitudinal axis of the anchor, thus biasing the electrodes against the vessel wall.

Figure 16A:
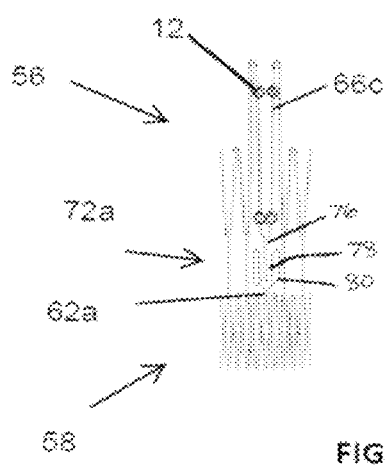
FIG. 16A is flattened view of a portion of a second variation of the anchor of FIG. 11A.
Figure 16B:
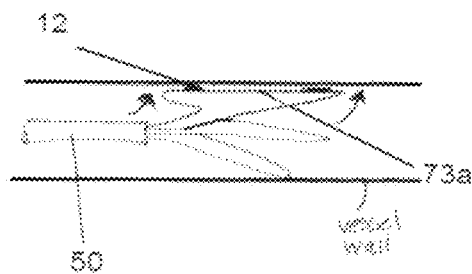
FIG. 16B schematically shows the first portion of anchor of FIG. 16A deployed within a vessel to position electrodes in contact with the vessel wall for mapping.
Figure 17A:
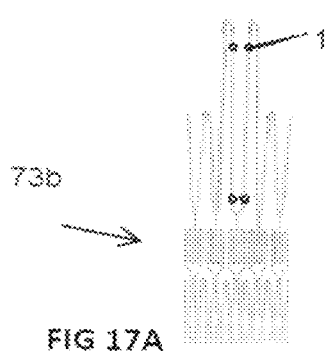
FIG. 17A is flattened view of a portion of a third variation of the anchor of FIG. 11A.
Figure 17B:
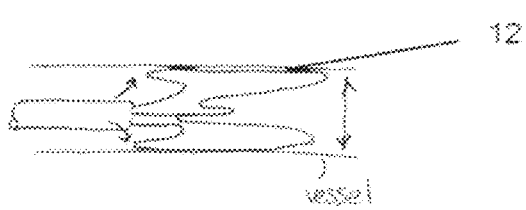
FIG. 17B schematically shows the first portion of anchor of FIG. 17A deployed within a vessel to position electrodes in contact with the vessel wall for mapping.

In the FIG. 17A/17B embodiment, an expansion section 73b is incorporated by adding the expansion feature of FIG. 16A to each of the struts 72, 73 of the third embodiment, allowing each proximal peak of the first portion 56 of the anchor, to more fully expand into contact with the surround vessel walls.

In other embodiments, the array and anchor system 210 of the third embodiment may be modified for acute use, such as to control heart rate or blood pressure through sympathetic and/or parasympathetic control of the autonomic nervous system during surgery or treatment of acute heart failure. In this type of embodiment, the second portion 58 of the anchor 30b may be eliminated, the struts 72 are instead mounted to the distal end of a catheter, with the first portion 56 of the anchor extends from the struts 72 as with the third embodiment. In use of this modified embodiment, the electrode and array are collapsed within a sheath and carried to the target stimulation site by advancing the catheter and surrounding sheath to the target site. The electrodes are in electrical communication with a pulse generator located outside the body. The anchor is expanded to cause the first portion 56 to bias the electrodes against the vessel wall, allowing for acute neurostimulation of targets outside the vasculature. Once the neuromodulation procedure has ended, the anchor is collapsed into a sheath, and the catheter is withdrawn to remove the anchor and array from the patient.

The third embodiment is one exemplary configuration of an anchor integrating both a mechanism for biasing the electrodes against the vessel for mapping as well as a mechanism for chronically anchoring the electrodes at the chosen site. However it should be understand that the first and second anchor portions might have different configurations or strut patterns than those shown. In some such alternatives, the first and second portions might have the same strut pattern, with the first section formed of thinner struts or coated with a lubricious materials allowing for repositioning without damaging the vessel wall. Moreover, while the third embodiment shows the chronic anchoring portion as proximal to the mapping anchoring portion, these portions may be referenced, with the chronic anchoring portion remaining compressed within a distal tip (such as tip 52) while the mapping portion is expanded upon withdrawal of the sheath.

FIG. 18 shows an alternative substrate 14 and electrode 12 configuration that may be used for transvascular stimulation. FIG. 19 schematically shows the FIG. 18 embodiment in a curled position within a vessel. FIG. 20 is similar but does not show the vessel. In this embodiment, the substrate may be deployed within the vessel in a rolled or spiral configuration. The substrate may be anchored in the vessel using an expandable anchor similar to those described herein, or expandable resilient baffles or expansion elements may be mounted to or molded into the substrate material.

The disclosed electrodes may be utilized for transvenous electrical stimulation from within the superior vena cava (SVC) or internal jugular vein to the vagus nerve to achieve reduction in blood pressure and heart rate, such as for treatment of congestive heart failure or other conditions.

All prior patents and applications referred to herein, including for purposes of priority, are incorporated by reference for all purposes.

It should be recognized that a number of variations of the above-identified embodiments will be obvious to one of ordinary skill in the art in view of the foregoing description. Moreover, it is contemplated that aspects of the various disclosed embodiments may be combined to produce further embodiments. Accordingly, the invention is not to be limited by those specific embodiments and methods of the present invention shown and described herein. Rather, the scope of the invention is to be defined by the following claims and their equivalents.

We claim:

1. A method of positioning an electrode array at an optimal stimulation site within a blood vessel, comprising: providing an expandable anchor having a first portion, a second portion, and a plurality of electrodes on the first portion, each of the first and second portions having a compressed position and an expanded position; with the first and second portions in the compressed position, positioning the anchor within a blood vessel; at a first location within the blood vessel, maintaining the second portion of the anchor in the compressed position while expanding the first portion to the expanded position, wherein expanding the first portion biases the electrodes in contact with walls of the blood vessel; performing a mapping procedure using the electrodes at the first location; after performing the mapping procedure, repositioning the anchor to place the electrodes at a second location different from the first location, wherein repositioning the anchor includes placing the electrodes into contact with the walls of the blood vessel at the second location while maintaining the second portion in the compressed position; performing a mapping procedure using the electrodes at the second location; and after performing a mapping procedure at the second location, expanding the second portion into contact with the walls of the blood vessel to chronically retain the electrodes at the second location.

2. The method of claim 1, wherein repositioning the anchor includes moving the first portion of the anchor to the compressed position, moving the anchor to the second location, and then moving the first portion of the anchor to the expanded position.

3. The method of claim 1, wherein the first portion of the anchor in the expanded position imparts first radial expansion forces against the blood vessel wall, wherein the second portion of the anchor in the expanded position imparts second radial expansion forces against the blood vessel wall, and wherein the second radial expansion forces are greater than the first radial expansion forces.

4. The method of claim 3, wherein moving the second portion of the anchor to the expanded position distends the blood vessel walls in a radially outward direction, and wherein moving the first portion of the anchor to the expanded position does not distend the blood vessel walls in a radially outward direction.

5. The method of claim 1, wherein expanding the first portion of the anchor while maintaining the second portion in the compressed position comprises releasing the first portion of the anchor from a sheath while maintaining the second portion of the anchor in a compressed position within the sheath, and wherein expanding the second portion of the anchor comprises releasing the second portion of the anchor from the sheath.

6. The method of claim 1 wherein expanding the second portion of the anchor comprises expanding the second portion without displacing the electrodes from their electrode locations.

7. The method of claim 2, wherein expanding the first portion of the anchor while maintaining the second portion in the compressed position comprises releasing the first portion of the anchor from a sheath while maintaining the second portion of the anchor in a compressed position within the sheath, wherein repositioning the anchor includes positioning the first portion in a compressed position within the sheath, and wherein expanding the second portion of the anchor comprises releasing the second portion of the anchor from the sheath.

8. A method of anchoring an electrode array within a blood vessel, comprising the steps of:

providing an implant comprising an anchor, a lead extending from the anchor and having at least one conductor extending therethrough, and a flex circuit coupled to the anchor, the flex circuit comprising a flexible insulative substrate, a plurality of electrodes carried by the substrate, and a plurality of conductive traces carried by the substrate, each trace electrically coupled to an electrode and a conductor; with the anchor in a radially compressed position, percutaneously introducing the implant into a patient's vasculature; positioning the implant at a target site in a blood vessel; causing the anchor to expand at the target site to a radially expanded position, thereby placing the electrodes into contact with a wall of the blood vessel; after causing the anchor to expand: performing a mapping procedure at the target site; and positioning a second anchor in a radially compressed position within a lumen of the anchor; and expanding the second anchor to a radially expanded position to chronically retain the electrodes in contact with the wall of the blood vessel.

9. The method of claim 8, wherein performing a mapping procedure at the target site includes performing mapping procedures with the electrodes at one or more sites within the blood vessel, and selecting one of said sites as the target site.

10. The method of claim 8, wherein expanding the second anchor to the radially expanded position chronically retains the first anchor against the blood vessel wall.

11. The method of claim 8, further including:
prior to positioning the implant at the target site, using a member detachably coupled to the anchor to position the implant at a first site in the blood vessel;
performing a mapping procedure at the first site;
manipulating the member to move the implant from the first site to a second site;
wherein performing the mapping procedure at the target site comprises performing mapping at the second site and determining the second site to be the target site; and
wherein the method further includes, with the anchor at the target site, detaching the member from the anchor.

\* \* \* \* \*